(12) United States Patent
Bellini et al.

(10) Patent No.: US 6,251,876 B1
(45) Date of Patent: Jun. 26, 2001

(54) AUTOCROSS-LINKED HYALURONIC ACID AND RELATED PHARMACEUTICAL COMPOSITIONS FOR THE TREATMENT OF ARTHROPATHIES

(75) Inventors: Davide Bellini, Padua; Annamaria Paparella, Bari; Michael O'Regan, Padua; Lanfranco Callegaro, Vicenza, all of (IT)

(73) Assignee: Fidia, S.p.A., Abano Terme (IT)

( * ) Notice: Subject to any disclaimer, the term of this patent is extended or adjusted under 35 U.S.C. 154(b) by 0 days.

(21) Appl. No.: 09/202,817
(22) PCT Filed: Jun. 20, 1997
(86) PCT No.: PCT/EP97/03238
   § 371 Date: Jun. 25, 1999
   § 102(e) Date: Jun. 25, 1999
(87) PCT Pub. No.: WO97/49412
   PCT Pub. Date: Dec. 31, 1997

(30) Foreign Application Priority Data

Jun. 21, 1996 (IT) .............................................. PD96A0163

(51) Int. Cl.[7] ...................................................... A61K 31/70
(52) U.S. Cl. .............................................. 514/54; 536/55.1
(58) Field of Search ................................... 536/55.1, 55.3; 514/54

(56) References Cited

FOREIGN PATENT DOCUMENTS

WO 89/10941 * 11/1989 (WO) .

* cited by examiner

*Primary Examiner*—Elli Peselev
(74) *Attorney, Agent, or Firm*—Birch, Stewart, Kolasch & Birch LLP; Leonard R. Svensson

(57) ABSTRACT

The present invention relates to compositions containing an autocross-linked form of hyaluronic acid as a first component in a mixture with a second component noncross-linked hyaluronic acid, and possibly also in combination with another pharmacologically active substance. These compositions can be used in the treatment of arthropathies due to their unique viscoelastic properties.

8 Claims, 17 Drawing Sheets

AUTOCROSS-LINKED HYALURONIC ACID AND RELATED PHARMACEUTICAL COMPOSITIONS FOR THE TREATMENT OF ARTHROPATHIES

SUMMARY OF THE INVENTION

The present invention relates to compositions containing an autocross-linked form of hyaluronic acid alone or as a first component in mixture with a second component noncross-linked hyaluronic acid, and possibly also in combination with another pharmacologically active substance. These compositions can be used in the treatment of arthropathies due to their unique viscoelastic properties.

BACKGROUND OF THE INVENTION

Hyaluronic acid (HA) is a naturally occurring polysaccharide of the glycosaminoglycan family which is present in particularly high concentration in the cartilage and synovial fluid of articular joints. It has been shown that synovial fluid acts as a viscous liquid at low shear (corresponding to the slowly moving joint) but shows an elastic behaviour at high shear (corresponding to the rapidly moving joint) (Balazs E. A., Univ. of Michigan, Med. Ctr. J. (Special Arthritis Issue), December 1968, 255). In patients with arthropathies such as osteoarthritis and rheumatoid arthritis, the viscoelastic properties of synovial fluid are compromised and this has been demonstrated to reflect a decrease of the viscoelastic contribution given by the HA component (Kobayashi Y. et al, Biorheology, 1994, 31, 235–244). This is clearly evident from FIG. 1 which shows the Theological profiles of synovial fluid from the joints of healthy volunteers and osteoarthritic donors ("The Rheological and Biological Function of Hyaluronic Acid," E. A. Balazs, D. A. Gibbs, in Chemistry and Molecular Biology of the Intercellular Matrix, ed. by E. A. Balazs, Academic Press, 1970). In normal synovial fluid, unlike in the case of osteoarthritis, viscoelasticity values are high and G' and G" cross each other. The existence of this crossover point is linked not only to the concentration of HA (2–4 mg/ml), but also, and above all, to its high molecular weight (about 4–5 million). In osteoarthritic subjects, on the other hand, there is both degradation of the hyaluronic acid, with consequent lowering of its molecular weight, and a decrease in its concentration (1–2 mg/ml).

Administration of highly purified, exogenous HA by intraarticular injection has been shown to be effective in the treatment of osteoarthritis. This is due not only to the unique viscoelastic properties of HA but also to its potential pharmacological properties. In fact, the commercial HA-based products which are currently marketed for the treatment of osteoarthritis by intra-articular injection reflect two schools of thought concerning the mode of action of HA in the treatment of these pathologies. There is strong evidence that unmodified HA exhibits pharmacological activity in addition to provoking a transient re-establishment of the viscoelastic properties of the synovial fluid (G. Abatangelo and M. O'Regan, Eur. J. Rheumatol. Inflamm., 1995, 15, 1:9–16; P. Ghosh, Clin Exp. Rheumatol., 1993, 12, 1–8; R. K. Strachan et al, An. Rheum. Dis., 1990, 49:949–952). On the other hand, manufacturers of chemically cross-linked HA derivatives promote the hypothesis that these derivatives act by solely mechanical means (E. A. Balazs and J. L. Denlinger, J. Rheumatology, 1993, vol. 20, supplement 39: 3–9).

Other forms of arthropathy besides osteoarthritis may result from modification of the viscoelastic properties of the synovial fluid of the articular joints which may occur as a result of particular mechanical or surgical operations carried out on the joint such as immobilization following joint distortion or fracture repair and joint arthroscopy. In the treatment of the functional consequences of these interventions, the lubricating potential of HA or derivatives thereof may be more pertinent than the long-term pharmacological effects of the compounds. In addition, HA is known to have a rapid turnover in the joint (Brown T. J. et al, Exp. Physiol., 1991, 76, 125–134; Fraser J. R. E. et al.; Semin. Arthritis Rheum., 1993, 22 (Suppl. 1), 9–17; Laurent U. B. G. et al., Matrix, 1992, 12, 130–6). Therefore, a further objective of the formulations described in the present invention is to increase the residence time of exogenous HA which is injected into the joints for treatment of arthropathies.

OBJECTS OF THE INVENTION

Therefore, it is an object of the present invention to provide new hyaluronic acid (HA)- and/or autocross-linked polysaccharide (ACP)-based compositions, possibly together with a suitable pharmaceutical excipient or carrier and/or drug for intraarticular use, which compositions exhibit appropriate viscoelastic properties for the treatment of arthropathies.

It is another object of the present invention to provide compositions which act as reservoirs of native HA.

Another object of the present invention is to provide a method for the treatment of arthropathies by delivering an HA- and/or ACP-based composition which exhibits appropriate viscoelastic properties and residence time within the joint and which is administered in an effective amount to a patient in need thereof.

The foregoing objects and others are accomplished in. accordance with the present invention by providing one of the following combinations:

1. an autocross-linked form of hyaluronic acid alone;
2. or an autocross-linked form of hyaluronic acid as a first component in mixtures containing, as a second component, hyaluronic acid and/or a pharmaceutically active drug for intraarticular use.

BRIEF DESCRIPTION OF DRAWINGS

The invention is further illustrated in the accompanying drawings wherein.

DETAILED DESCRIPTION OF THE INACTION

Figure 1:
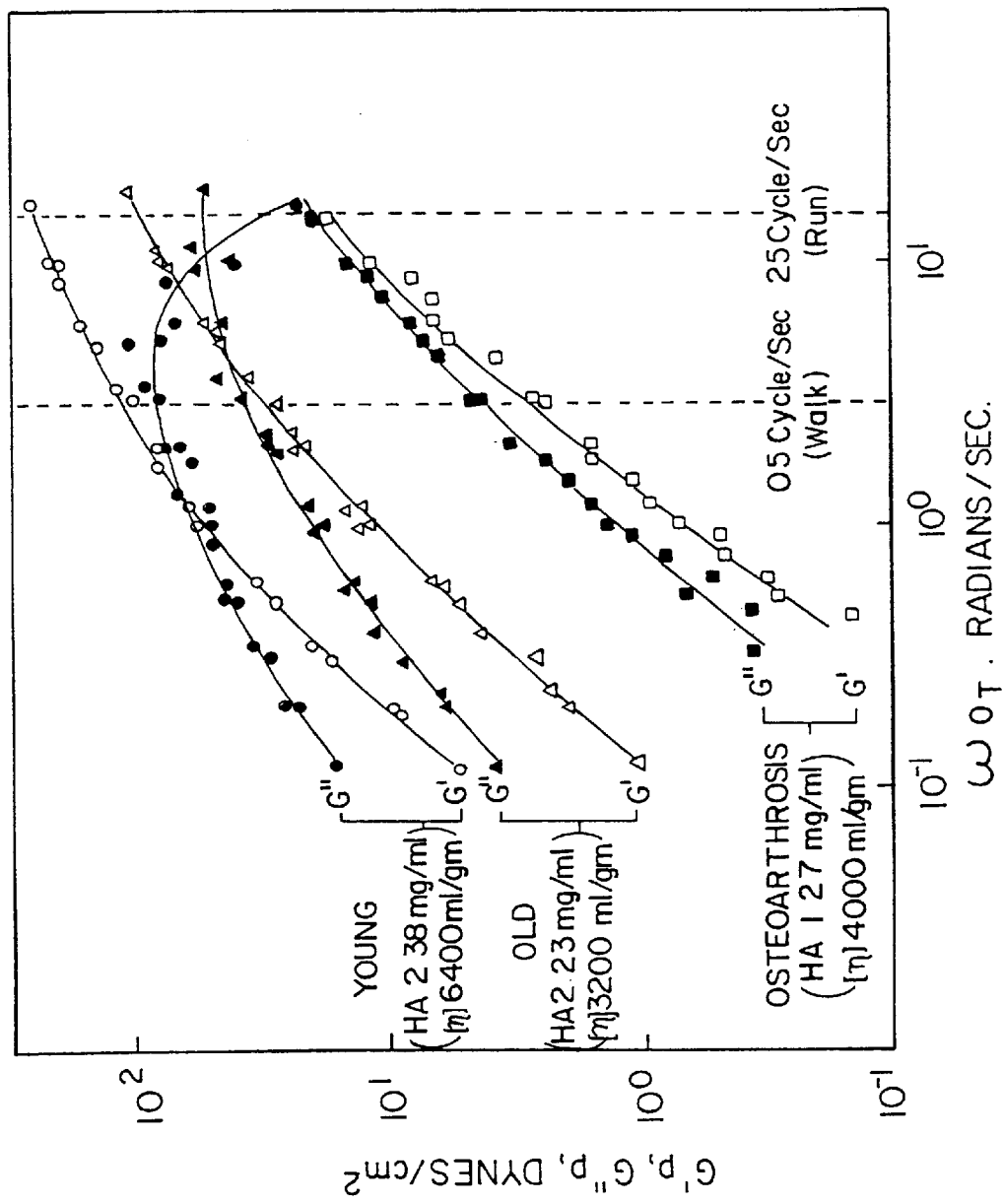
FIG. 1 shows viscoelastic spectra of human synovial fluid from young healthy donors, elderly healthy donors, and osteoarthritic donors.

It is an aim of the present invention to provide a new formulation able to improve the viscoelasticity and synovial residence time of exogenous HA which is injected into the joints for the treatment of arthropathies.

This formulation consists of autocross-linked HA, alone or as a first component in mixtures containing as a second component hyaluronic acid. In these formulations, the autocross-linked polysaccharide (ACP) is obtained through an autocross-linking process that leads to the formation of intra- and inter-chain ester bonds without introducing any foreign bridge between the polymer chains as described in EP 0341745 B1.

The ACP component can be synthesized from HA having a molecular weight in the range from 50 kDa to 5,000 kDa and must have a pharmaceutical grade purity and a level of cross-linking which ranges from 1% to 30% with respect to the carboxyl groups of the polymer.

Preferred examples of the ACP component include: ACP 5, ACP 10, ACP 15 and ACP 20 where the numbers 5, 10, 15 and 20 reflect the nominal level of cross-linking based on the stoichiometry of the chemical reaction.

These autocross-linked HA derivatives can, therefore, be used to advantage in the preparation of suspensions for the treatment of arthropathies due to their improved viscoelasticity with respect to native HA, which is released upon degradation of these autocross-linked derivatives. ACP HA derivatives therefore constitute ideal viscoelastic materials in addition to being a reservoir of native HA which is slowly released upon degradation resulting in a prolongation of the contact time of native HA with the joint tissues. The safety of these autocross-linked HA derivatives is also potentially better than HA derivatives produced by alternative cross-linking reactions since the native HA which is released by the degradation of ACP is metabolised by physiological metabolic pathways.

Moreover, taking into account the gel-like behaviour of ACP's in aqueous media (Mensitieri et al., Abstract, "12th European Conference on Biomaterials" Porto Portugal, Sep. 10–13, 1995), it is possible by blending HA with its ACP derivatives to obtain a wide range of systems which may combine viscoelastic and reservoir properties.

The non-ideal Theological properties of .ACP alone may be compensated for by preparing pharmaceutical compositions which are composed of mixtures of ACP and unmodified HA at varying ratios of the two components according to the condition of the patient and to the joint to be treated.

The relative proportions of the ACP and HA employed in the formulations of the present invention generally include ACP/HA in relative amounts of about 95:05 to about 05:95. Preferred ratios for the ACP/HA formulations include ACP/HA at ratios of about 75:25 to about 25:75.

The ACP/HA formulations of the present invention may be made into pharmaceutical compositions and may be combined with appropriate pharmaceutically active drugs, such as anaesthetics, antibiotics, steroidal and non-steroidal antiinflammatory drugs, hormonal-type antiinflammatory agents, such as somatostatina, epitheliotrophic vitamins, cytokines such as IL-1 and IL-6, cytokine receptors, growth factors such as FGF and acceptable excipients. Moreover, it is possible to use pharmaceutical compositions starting from mixtures of ACP and HA wherein the HA is salified with silver, copper, zinc and calcium salts. These pharmaceutical compositions may be formulated into preparations in semi-solid or liquid forms for intraarticular use.

The total quantity of HA, either in the form of ACP or HA, is in the range of 3–50 mg. A suitable dosage is that which contains a total amount of HA contained in the pharmaceutical compositions, either in the form of ACP or HA, of 20 mg in a final volume of 2 ml of suitable pharmaceutical excipient.

1. Autocross-Linked Polysaccharide (ACP) Product

The ACP derivatives utilized in the present composition are autocross-linked derivatives of hyaluronic acid hyaluronic acid. In these derivatives, all or a part of the carboxyl groups of the hyaluronic acid are esterified with hydroxyl groups of the same molecule and/or of different hyaluronic acid (HA) molecules, thus forming lactone or intermolecular ester bonds. These "inner" esters of HA, in which there is no intervention by OH groups of other alcohols, can also be defined as "auto-crosslinked polysaccharides", since the formation of a mono- or polymolecular cross-link is the consequence of the above-mentioned internal esterification. The adjective "cross-linked" refers to the crosswise connections between the carboxyls and hydroxyls of the polysaccharide molecules.

The inner esters can be total or partial, depending on whether all or only part of the carboxy functions are esterified in the above manner. In the partial inner esters, further carboxy functions can be either totally or partially esterified with monovalent or polyvalent alcohols, thus forming "external" ester groups, and in the partial esters of both these ester groups, the non-esterified carboxy functions may be free or salified with metals or organic bases.

The inner esters used in the present invention can be prepared by the method described in EP 0 341 745 B1 which involves the activation of the carboxy groups by the addition of substances capable of inducing such activation. The unstable intermediate products obtained from the activation reaction separate spontaneously, either after the addition of catalysts and/or following a rise in temperature, forming the above-mentioned inner ester bonds with hydroxyls of the same or other HA molecule. According to the degree of inner esterification desired, either all or an aliquot part of the carboxy functions are activated (the aliquot part being obtained by using an excess of activating substances or by suitable dosing methods).

The carboxy groups to be converted into inner ester groups can be activated starting from polysaccharides containing free carboxy groups, or, preferably, from polysaccharides containing salified carboxy groups, for example metal salts, preferably alkaline or alkaline earth metals, and above all with quaternary ammonium salts, such as those descried hereafter. Salts with organic bases such as amines can however also be used as starting substances.

The number of carboxy functions to be converted into inner esters is in proportion to the number of activated carboxy functions and this number depends on the quality of the activating agent used. In order to obtain total inner esters therefore, an excess of activating agents should be used, while in the case of partial esters, the quantity of this agent should be dosed according to the degree of esterification desired.

The carboxy groups which are still free or salified after the cross-linking reaction can be exchanged in order to obtain opportune salts or can be esterified with monovalent or polyvalent alcohols thus obtaining mixed esters, partly cross-linked and partly externally esterified. Of course, partial esterification with alcohols can be effected before activation of part of the carboxy groups and subsequent conversion into inner esters.

In the produced crosslinked products, the remaining free carboxy groups or those in the form of salts can be partially or totally esterified with mono- or polyvalent alcohols, thus obtaining esters mixed with bonds which are in part internal and in part external. The alcohols used for this esterification correspond to those described hereafter and from which mixed esters are derived.

According to EP 0 216 453 A1, the external esters can be advantageously prepared by starting with quaternary ammonium salts with an etherifying agent in an aprotic solvent, such as dialkylsulfoxides, dialkylcarboxylamides, such as in particular lower alkyl dialkylsulfoxides with a maximum of 6 carbon atoms, particularly dimethylsulfoxide, and the lower alkyl dialkylamides of lower aliphatic acids, such as dimethyl or diethyl formamide or dimethyl or diethyl acetamide. Reaction should be effected preferably within a temperature range of between about 25° and 75°, for example at about 30°. Esterification is effected preferably by gradually adding the etherifying agent to the above-said ammonium salt dissolved in one of the solvents mentioned, for example in dimethylsulfoxide.

In the inner esters, the carboxy groups still left intact can be salified with organic or inorganic bases. The choice of bases for the formation of such salts is based on the intended use of the product. The inorganic salts are preferably those of alkaline metals, such as sodium or potassium salts or ammonium salts, cesium salts, salts of alkaline earth metals, such as calcium, magnesium or aluminum.

The salts of organic bases are especially those of aliphatic, araliphatic, cycloaliphatic or heterocyclic amines. The ammonium salts of this type may derive from therapeutically acceptable, but inactive, amines, or from amines with a therapeutic action. Of the former, special consideration should be given to aliphatic amines, for example, mono, di and trialkylamines, with alkyl groups with a maximum of 18 carbon atoms, or arylalkylamines with the same number of carbon atoms in the aliphatic part and where aryl means a benzene group possibly substituted by between 1 and 3 hydroxy groups. As therapeutically acceptable amines, but not active in themselves, cyclic amines are very suitable, such as alkylene amines with rings of between 4 and 6 carbon atoms, possibly interrupted in the ring by heteroatoms, such as oxygen, sulphur and nitrogen, such as piperidine, morpholine or piperazine, or may be substituted for example by amino or hydroxy functions, as in the case of aminoethanol, ethylene diamine or choline.

In the ACP derivatives which also have carboxy functions esterified with monovalent or polyvalent alcohols, whether these functions be present in the starting materials of the above-mentioned procedure, or whether they be introduced at the end of the procedure, the alcohols may belong to the aliphatic, araliphatic, alicyclic or heterocyclic series.

Alcohols of the aliphatic series for use as esterifying components are for example those with a maximum of 34 carbon atoms, which can be saturated or unsaturated and which can possibly also be substituted by other free functional or functionally modified groups, such as amino, hydroxyl, aldehydo, keto, mercapto, carboxy groups or by groups deriving from these, such as hydrocarbyl or dihydrocarbylamino groups (here and hereafter meaning by the term "hydrocarbyl" not only monovalent radicals of carbohydrates for example type $C_nH_{2n+1}$, but also bivalent or trivalent radicals, such as "alkylenes" $C_nH_{2n}$ or "alkylidenes" $C_nH_{2n}$), ether or ester groups, acetal or ketal groups, thioether or thioester groups, and esterified carboxy groups or carbamidic and substituted carbamidic groups by one or two hydrocarbyl groups, by nitrite groups or halogens. Of the above groups containing hydrocarbyl radicals, these should preferably be lower aliphatic radicals, such as alkylic, with a maximum of 6 carbon atoms. Such alcohols may then be interrupted in the carbon atom chain by heteroatoms, such as atoms of oxygen, nitrogen and sulfur.

It is preferable to choose alcohols substituted with one or two of the above-said functional groups. Alcohols of the above group to be preferred for the purposes of the present invention are those with a maximum of 12 and especially 6 carbon atoms and in which the hydrocarbyl radicals in the above-said amino, ether, ester, thioether, thioester, acetal, ketal groups represent alkyl groups with a maximum of 4 carbon atoms, and also in the esterified carboxy groups or substituted carbamidic groups or hydrocarbyl groups are alkyls with the same number of carbon atoms, and in which the amino or carbamidic groups may be alkylene amine or alkylene carbamidic groups with a maximum of 8 carbon atoms. Of these alcohols, of particular interest are those which are saturated and unsubstituted such as methyl, ethyl, propyl, isopropyl alcohols, n-butyl alcohol, isobutyl alcohol, tert-butyl alcohol, amyl alcohols, pentyl, hexyl, octyl, nonyl and dodecyl alcohols and above all those with a linear chain, such as n-octyl and n-dodecyl alcohols. Of the substituted alcohols of this group, preferred are: bivalent alcohols such as ethylene glycol, propylene glycol, butylene glycol, trivalent alcohols such as glycerin, aldehyde alcohols such as tartronic alcohol, carboxy alcohols such as lactic acids, for example glycolic acid, malic acid, tartaric acids, citric acid, aminoalcohols, such as aminoethanol, aminopropanol, n-aminopropanol, n-aminobutanol and their dimethyl and diethyl derivatives in the amine function, choline, pyrrolidinylethanol, piperidinylethanol, piperazinylethanol and the corresponding derivatives of n-propyl or n-butyl alcohols, monothioethyleneglycol and its alkyl derivatives, for example the ethyl derivative in the mercapto function.

Of the higher aliphatic saturated alcohols, the following are examples: cetyl alcohol and myricyl alcohol, but of special importance for the purposes of the present invention are the higher unsaturated alcohols with one or two double bonds, such as especially those contained in many essential oils and having affinity with terpenes, such as citronellol, geraniol, nerol, nerolidol, linalool, farnesol, phytol. Of the lower unsaturated alcohols, the ones to be considered are allyl alcohol and propargyl alcohol.

Of the araliphatic alcohols, preferred are those with only one benzene residue and in which the aliphatic chain has a maximum of 4 carbon atoms and in which the benzene residue may be substituted by between 1 and 3 methyl or hydroxy groups or by halogen atoms, especially by chlorine, bromine, iodine, and in which the aliphatic chain may be substituted by one or more functions chosen from the groups comprising free amino groups or mono or dimethyl groups or by pyrrolidine or piperidine groups. Of these alcohols, most preferred are benzyl alcohol and phenethyl alcohol.

Alcohols of the cycloaliphatic or aliphatic cycloaliphatic series may derive from mono or polycyclic carbohydrates, may preferably have a maximum of 34 carbon atoms, may be unsubstituted and may contain one or more substituents, such as those mentioned above for the aliphatic alcohols. Of the alcohols derived from single-ringed cyclic carbohydrates, preferred are those with a maximum of 12 carbon atoms, the rings having preferably between 5 and 7 carbon atoms, which may be substituted for example by between one and three lower alkyl groups, such as methyl, ethyl, propyl, or isopropyl groups. As alcohols specific to this group, cyclohexanol, cyclohexanediol, 1,2,3 cyclohexanetriol and 1,3,5 cyclohexanetriol (phloroglucitol), inositol, should be mentioned, as well as the alcohols deriving from p-menthane, such as carvomenthol, menthol, α and γ-terpineol, 1-terpinenol, 4-terpinenol and piperitol, or the mixture of these alcohols as "terpineol", 1,4-and 1,8-terpin. Of the alcohols deriving from carbohydrates with condensed rings, for example those of the thujane, pinane or camphane group, useful also are thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as the sexual hormones and their synthetic analogues, and in particular corti-costeroids and their derivatives. Thus it is possible to use for example: cholesterol, dihydrocholesterol, epidihydrocholesterol, coprostanol, epicoprostanol, sitosterol, stigmasterol, ergosterol, cholic acid, cdeoxycholic acid, lithocholic acid, estriol, estradiol, equilenin, equilin and their alkyl derivatives, as well as the ethynyl or propynyl derivatives in position 17, for example 17-α-ethynyl-estradiol or 7-α-methyl-17-α-ethynyl-estradiol, pregnenolone, pregnanediol, testosterone and its derivatives, such as 17-α-methyltestosterone, 1,2-dehydro-testosterone and 17-α-methyl-1,2-dehydrotestosterone, alkynyl derivatives in position 17 of testosterone and 1,2-dehydrotestosterone, such as 17-α-ethynyltestosterone, 17-α-propynyltestosterone, norgestrel, hydroxyprogesterone, corticosterone, deoxycorticosterone, 19-nortestosterone, 19-nor-17-α-methyltestosterone and 19-nor-17-α-ethynyl-testosterone, cortisone, hydrocortisone, prednisone, prednisolone, fludrocortisone, dexamethasone, beta-methasone, paramethasone, flumethasone, fluocinolone, fluprednylidene, clobetasol, beclomethasone, aldosterone, desoxycorticosterone, alfaxalone, alfadolone, bolasterone.

Useful esterifying components for the esters of the present invention are genies, (aglycons) of cardioactive glycosides, such as digitoxigenin, gitoxigenin, digoxigenin, strophanthidin, tigogenin, saponins.

Other alcohols to be used according to the invention are vitamin alcohols such as axerophthol, vitamins $D_2$ and $D_3$, aneurine, lactoflavine, ascorbic acid, riboflavine, thiamine, pantothenic acid.

Heterocyclic alcohols may be considered to be derivatives of the above-said cycloaliphatic or aliphatic-cycloaliphatic alcohols, if their linear or cyclic chains are interrupted by one or more, for example between one and three ethero atoms chosen from the group formed by —O—, —S—, —N and —NH and in these there may be one or more unsaturated bonds for example double bonds, particularly between one and three, thus including also heterocyclic compounds with aromatic structures. The following are specific useful examples: furfuryl alcohol, alkaloids and derivatives such as atropine, scopolamine, cinchonine, cinchonidina, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, acetophenazine, fluphenazine, N-hydroxyethylpromethazine chloride; thioxanthene drugs such as flupenthizol and clopenthixol; anticonvulsivants such as meprophendiol, antipsychotics such as opipramol; antiemetics such as oxypendil; analgesics such as carbetidine and phenoperidine and methadol; hypnotics such as etodroxizine; anorexics such as benzhydrol and diphemethoxidine; mild tranquilizers such as hydroxyzine; muscle relaxants such as cinnamedrine, diphylline, mephenesin, methocarbamol, chlorphenesin, 2,2-diethyl-1,3-propanediol, guaifenesin, idrocilamide; coronary vasodilators such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatics and antiinflammatories such as tiaramide; sulfamides such as 2-p-sulfanylanilinoethanol.

2. The Hyaluronic Acid

In the present invention, hyaluronic acid (HA) serves as the starting material for making the ACP derivatives, or as a second component in combination with the ACP derivatives. The cross-linked HA may use, as starting substrate, any natural or synthetic HA.

The substrate of hyaluronic acid can be of any origin, such as acids extracted from the above natural starting materials, for example from cocks' combs. The ACP/HA formulations of the present invention employ hyaluronic acid isolated from either bacterial (WO 95/04132) or animal sources (EP 0138572; WO 92/18543) or hyaluronic acid produced by in-vitro enzymatic synthesis (WO 95/24497). According to the invention, it is preferable to use hyaluronic acids constituting molecular fractions of the integral acids obtained directly by extraction of organic materials with a wide range of molecular weights, for example between 90%–80% and 0.2% of the molecular weight of the integral acid, preferably between 5% and 0.2%. These fractions can be obtained by various procedures described in literature, and that is with hydrolyzing, oxidizing or enzymatic chemical agents or physical procedures, for example mechanical or irradiation procedures, and often during the same purification procedures, primordial extracts may be formed. Separation and purification of the molecular fractions obtained comes about by means of known techniques, such as by molecular filtration. One purified HY fraction suitable to be used according to the invention is for example the one known as "noninflammatory-NIF-NaHA sodium hyaluronate", described by Balazs in the pamphlet "Healon" —A guide to its use in Ophthalmic Surgery—D. Miller & R. Stegmann, eds. John Wiley & Sons N.Y 81983: p.5.

Also particularly important as starting materials for the ACP esters are two purified fractions which can be obtained from hyaluronic acid, for example the one extracted from cocks' combs, known by the names of "Hyalastine" and "Hyalectin". The fraction Hyalastine has an average molecular weight of about 50,000 to 100,000 while the fraction Hyalectin has an average molecular weight of about 500,000 to 730,000. One combined fraction of these two fractions has also been isolated and characterized as having an average molecular weight of between about 250,000 and about 350,000. This combined fraction can be obtained with a yield of 80% of the total hyaluronic acid available in the particular starting material, while the fraction Hyalectin can be obtained with a yield of 30% and the fraction Hyalastine with a yield of 50% of the starting HY. The preparation of these fractions is described in the above-mentioned European patent publication No. 0138572A3.

The invention is illustrated by the following illustrative examples, without these in any way limiting its scope.

3. Preparation of ACP Derivatives

EXAMPLE 1
PREPARATION OF CROSS-LINKED HYALURONIC ACID (HY)

Product Description:
  1% of carboxy groups used in internal esterification.
  99% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.01 g (0.1 mEq) of triethylamine are added and the resulting solution is agitated for 30 minutes.

A solution of 0.026 g (0.1 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

3.97 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 2
PREPARATION OF CROSS-LINKED HYALURONIC ACID (HY)

Product Description:
  5% of carboxy groups used in internal esterification.
  95% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.051 gr (0.5 mEq) of triethylamine are added and the resulting solution is agitated for 30 minutes.

A solution of 0.128 gr (0.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.95 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 3
PREPARATION OF CROSS-LINKED HYALURONIC ACID (HY)

Product Description:
  10% of carboxy groups used in internal esterification.
  90% of carboxy groups salified with sodium.

6.21 g of HY tetrabutylammonium salt with a molecular weight of 620,000 corresponding to 10 mEq of a monomeric unit are solubilized in 248 ml of DMSO at 25° C., 0.101 gr (1.0 mEq) of triethylamine is added and the resulting solution is agitated for 30 minutes.

A solution of 0.255 gr (1.0 mEq) of 2-chloro-1-methyl-pyridinium iodide in 60 ml of DMSO is slowly added drop by drop over a time interval of I hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.93 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 4
PREPARATION OF CROSS-LINKED HYALURONIC ACID (HY)

Product Description:
  25% of carboxy groups used in internal esterification.
  75% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.253 g (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.85 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 5
PREPARATION OF CROSS-LINKED HYALURONIC ACID (HY)

Product Description:
  50% of carboxy groups used in internal esterification.
  50% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.506 g (5.0 mEq) of triethylamine are added and the resulting solution is agitated for 30 minutes.

A solution of 1.28 gr (5 mEq) of 2-chloro-1-methyl-pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.65 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 6
PREPARATION OF CROSS-LINKED HYALURONIC ACID (HY)
Product Description:
- 75% of carboxy groups used in internal esterification.
- 25% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.759 gr (7.5 mEq) of triethylamine is added and the resulting solution is agitated for 30 minutes.

A solution of 1.92 gr (7.5 mEg) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.54 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 7
PREPARATION OF CROSS-LINKED HYALURONIC ACID (HY)
Product Description:
- 100% of carboxy groups used in internal esterification.

6.21 g of HY tetrabutylammonium salt with a molecular weight of 70,000 corresponding to 10 mEq of a monomeric unit are solubilized in 248 ml of DMSO at 25° C, 1.012 gr (10 mEq) of triethylamine are added and the resulting solution is agitated for 30 minutes.

A solution of 2.55 gr (10 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is filtered and washed six times with 100 ml of acetone and lastly vacuum-dried for 24 hours at 30° C.

3.52 grs of the title compound are obtained. Quantitative determination of the ester groups is carried out according to the saponification method described on pp 169–172 of "Quantitative Organic Analysis Via Functional Groups" 4th Edition John Wiley and Sons Publication.

EXAMPLE 8
PREPARATION OF THE PARTIAL ETHYL ESTER OF CROSS-LINKED HYALURONIC ACID (HY)
Product Description:
- 25% of carboxy groups esterified with ethanol;
- 25% of carboxy groups used in internal esterification.
- 50% of carboxy groups salified with sodium.

6.21 g of HY tetrabutylammonium salt with a molecular weight of 170,000 corresponding to 10 mEq of a monomeric unit are solubilized in 248 ml of DMSO at 25° C., 0.390 gr (2.5 mEq) of ethyl iodide are added and the solution is kept for 12 hours at 30° C. 0.253 gr (2.5 mEq) of triethylamine are added and the solution is agitated for 30 minutes.

A solution of 0.639 g (2.5 mEg) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is slowly poured into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.84 grs of the title compound are obtained. Quantitative determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative Organic Analysis Via Functional Groups" 4th Edition John Wiley and Sons Publication.

EXAMPLE 9
PREPARATION OF THE PARTIAL ETHYL ESTER OF CROSS-LINKED HYALURONIC ACID (HY)
Product Description:
- 50% of carboxy groups esterified with ethanol;
- 25% of carboxy groups used in internal esterification.
- 25% of carboxy groups salified with sodium.

6.21 g of HY tetrabutylammonium salt with a molecular weight of 85,000 corresponding to 10 mEq of a monomeric unit are solubilized in 248 ml of DMSO at 25° C., 0.780 g (5.0 mEq) of ethyl iodide are added and the solution is kept for 12 hours at 30° C. 0.253 gr (2.5 mEq) of triethylamine are added and the solution is agitated for 30 minutes.

A solution of 0.639 g (2.5 mEq) of 2-chloro-1-methyl pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times in 100 ml of acetone/water 5:1 and three times with 100 ml of acetone and lastly vacuum-dried for 24 hours at 30° C.

3.87 grs of the title compound are obtained. Quantitative determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative Organic Analysis Via Functional Groups" 4th Edition John Wiley and Sons Publication.

EXAMPLE 10
PREPARATION OF THE ETHYL ESTER OF CROSS-LINKED HYALURONIC ACID (HY)

Product Description:
- 75% of carboxy groups esterified with ethanol;
- 25% of carboxy groups used in internal esterification.

6.21 g of HY tetrabutylammonium salt with a molecular weight of 170,000 corresponding to 10 mEg of a monomeric unit are solubilized in 248 ml of DMSO at 25° C, 1.17 gr (7.5 mEq) of ethyl iodide are added and the solution is kept for 12 hours at 30° C. 0.253 g (2.5 mEq) of triethylamine are added and the solution is agitated for 30 minutes.

A solution of 0.639 gr (2.5 mEq) of 2-chloro-1-methyl pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is filtered and washed five times with 100 ml of acetone and lastly vacuum-dried for 24 hours at 30° C.

3.91 grs of the title compound are obtained. Determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative organic Analysis Via Functional Groups" 4th Edition John Wiley and Sons Publication.

EXAMPLE 11
PREPARATION OF THE PARTIAL CORTISONE ESTER (C21) OF CROSS-LINKED HYALURONIC ACID (HY)

Product Description:
- 20% of carboxy groups esterified with cortisone.
- 25% of carboxy groups used in internal esterification.
- 55% of carboxy groups salified with sodium.

6.21 gr of HY tetrabutylammonium salt with a molecular weight of 70,000 corresponding to 10 mEq of a monomeric unit are solubilized in 248 ml of DMSO at 25° C. 0.85 gr (2 mEq) 21-bromo-4-pregnene-17-α-ol-3,11,20-trion and the resulting solution is kept for 24 hours at 30° C. 0.253 gr (2.5 mEq) of triethylamine are added and the resulting solution is agitated for 30 minutes.

A solution of 0.639 g (2.5 mEq) of 2-chloro-1-methyl-pyridinium iodide in 60 ml of DMSO is slowly added drop by drop over a time interval of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

4.5 grs of the title compound are obtained. Quantitative determination of cortisone, mild alkaline hydrolysis with a hydroalcoholic solution of $Na_2CO_3$ and extraction with chloroform, is carried out according to B. P.

Quantitative determination of the total ester groups is carried out according to the saponification method described on pp 169–172 of "Quantitative Organic Analysis Via Functional Groups" 4th Edition John Wiley and Sons Publication.

EXAMPLE 12
PREPARATION OF THE MIXED ETHANOL AND CORTISONE PARTIAL ESTER (C21) OF CROSS-LINKED HYALURONIC ACID (HY)

Product Description:
- 20% of carboxy groups esterified with cortisone (C21).
- 25% of carboxy groups esterified with ethanol.
- 25% of carboxy groups used in internal esterification.
- 30% of carboxy groups salified with sodium.

6.21 gr of HY tetrabutylammonium salt with a molecular weight of 85,000 corresponding to 10 mEq of a monomeric unit are solubilized in 248 ml of DMSO at 25° C. 0.39 gr (2.5 mEq) of ethyl iodide are added and the resulting solution is kept at 30° C. for 12 hours. 0.85 gr (2 mEq) of 21-bromo-4-pregnene-17-α-ol-3,11,20-trion are added and the resulting solution is kept at 30° C. for 24 hours. 0.253 gr (2.5 mEq) of triethylamine are added and the resulting solution is agitated for 30 minutes.

A solution of 0.639 g (2.5 mEq) of 2-chloro-1-methyl pyridinium iodide in 60 ml of DMSO is slowly added drop by drop over a period of 1 hour and the mixture is kept for 15 hours at 30° C.

A solution formed by 100 ml of water and 2.5 gr of sodium chloride is then added and the resulting mixture is then poured slowly into 750 ml of acetone, maintaining continual agitation. A precipitate is formed which is then filtered and washed three times with 100 ml of acetone/water 5:1 and three times with 100 ml of acetone and lastly vacuum-dried for 24 hours at 30° C.

4.41 grs of the title compound are obtained. Quantitative determination of cortisone, mild alkaline hydrolysis with a hydroalcoholic solution of $Na_2CO_3$ and extraction with chloroform, is carried out according to B. P.

Quantitative determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative Organic Analysis Via Functional Groups" 4th Edition John Wiley and Sons Publication.

EXAMPLE 13
PREPARATION OF THE MIXED ETHANOL AND CORTISONE ESTER (C21) OF CROSS-LINKED HYALURONIC ACID (HY)

Product Description:
- 20% of carboxy groups esterified with cortisone (C21).
- 70% of carboxy groups esterified with ethanol.
- 10% of carboxy groups used in internal esterification.

6.21 g of HY tetrabutylammonium salt with a molecular weight of 170,000 corresponding to 10 mEq of a monomeric unit are solubilized in 248 ml of DMSO at 25° C. 1.09 g (7 mEq) of ethyl iodide are added and the resulting solution is kept at 30° C. for 12 hours. 0.85 gr (2 mEq) of 21-bromo-4-pregnene-17-α-ol-3,11,20-trion and the resulting solution is kept at 30° C. for 24 hours. 0.101 gr (1.0 mEq) of triethylamine are added and the resulting solution is agitated for 30 minutes.

A solution of 0.255 g (1.0 mEq) of 2-chloro-1-methyl-pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

4.58 grs of the title compound are obtained. Quantitative determination of cortisone, mild alkaline hydrolysis with a hydroalcoholic solution of $Na_2CO_3$ and extraction with chloroform, is carried out according to B. P.

Quantitative determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative Organic Analysis Via Functional Groups" 4th Edition John Wiley and Sons Publication.

EXAMPLE 14
PREPARATION WITH KANAMYCIN OF THE SALT OF A CROSS-LINKED HYALURONIC ACID
Product Description:
- 25% of carboxy groups used in internal esterification.
- 75% of carboxy groups with kanamycin.

4.39 gr of partial tetrabutylammonium salt (25%) of hyaluronic acid corresponding to 10 mEq of a monomeric unit are solubilized in 248 ml of DMSO at 25° C., 0.253 gr (2.5 mEq) of triethylamine are added and the resulting solution is agitated for 30 minutes.

A solution of 0.639 g (2.5 mEq) of 2-chloro-1-methyl-pyridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml di acetone and lastly vacuum-dried for 24 hours at 30° C.

The precipitate is suspended in 400 ml of distilled water and cooled to 5° C. after which a solution obtained by solubilizing 1.1 gr of Kanamycin sulfate (7.5 mEq) in 25 ml of distilled $H_2O$ and eluting in a column containing 15 ml of quaternary ammonium resin (Dowex 1×8) OH— form is added, while agitation is maintained for 30 minutes. The resulting mixture is freeze-dried.

4.6 grs of the title compound are obtained. Quantitative determination of the ester groups is carried out according to the saponification method described on pp 169–172 of "Quantitative Organic Analysis Via Functional Groups" 4th Edition John Wiley and Sons Publication.

Microbiological quantitative determination of Kanamycin is carried out on *B. subtilis* 6633 in comparison to standard Kanamycin.

EXAMPLE 15
PREPARATION WITH AMIKACIN OF A CROSS-LINKED HYALURONIC ACID SALT
Product Description:
- 25% of carboxy groups used in internal esterification.
- 75% of carboxy groups with amikacin.

4.39 gr of partial tetrabutylammonium salt (25%) of hyaluronic acid corresponding to 10 mEq of a monomeric unit are solubilized in 248 ml of DMSO at 25° C, 0.253 gr (2.5 mEq) of triethylamine are added and the resulting solution is agitated for 30 minutes.

A solution of 0.639 gr (2.5 mEq) of 2-chloro-1-methyl-piridinium iodide in 60 ml of DMSO is slowly added drop by drop over a time interval of 1 hour and the mixture is kept for 15 hours at 30° C.

The resulting mixture is slowly poured into 750 ml of acetone, maintaining continual agitation. A precipitate is formed which is then filtered and washed five times with 100 ml of acetone and lastly vacuum-dried for 24 hours at 30° C.

The precipitate is suspended in 400 ml of distilled water and cooled to 5° C.

1.1 gr (7.5 mEq) of basic amikacin are added while under constant agitation for 30 minutes. The resulting mixture is freeze-dried.

4.8 grs of the title compound are obtained. Quantitative determination of the ester groups is carried out according to the saponification method described on pp 169–172 of "Quantitative Organic Analysis Via Functional Groups" 4th Edition John Wiley and Sons Publication.

Quantitative determination of amikacin is carried out microbiologically on *S. aureus* 29737, compared to standard Amikacin.

EXAMPLE 16
PREPARATION OF THE PARTIAL ETHYL ESTER OF CROSS-LINKED HYALURONIC ACID (HY)
Product Description:
- 50% of carboxy groups esterified with ethanol.
- 10% of carboxy groups used in internal esterification.
- 40% of carboxy groups salified with sodium.

6.21 gr of HY tetrabutylammonium salt with a molecular weight of 85,000 corresponding to 10 mEq of a monomeric unit are solubilized in 248 ml of DMSO at 25° C., 0.780 gr (5.0 mEq) of ethyl iodide are added and the solution is kept for 12 hours at 30° C. 0.118 gr (1 mEq) of pyridine chloride are added and the resulting solution is agitated for 30 minutes.

A solution of 0.16 g (1 mEq) of N-benzyl-N'-ethyl carbodiimmide in 20 ml of DMSO is slowly added drop by drop over a time interval of 1 hour and the mixture is kept for 45 hours at 30° C.

A solution is then added which is formed of 100 ml of water and 2.5 of sodium chloride and the resulting mixture is then poured slowly into 750 ml of acetone, maintaining continual agitation. A precipitate is formed which is then filtered and washed three times with 100 ml of acetone/$H_2O$ 5:1 and three times with 100 ml of acetone and lastly vacuum-dried for 24 hours at 30° C.

3.85 grs of the title compound are obtained. Quantitative determination of the ethoxy groups is carried out according to the method of R. H. Cundiff and P. C. Markunas (Anal. Chem. 33, 1028–1930 (1961)). Quantitative determination of the total ester groups is carried out according to the saponification method described on pp 169–172 of "Quantitative Organic Analysis Via Functional Groups" 4th Edition John Wiley and Sons Publication.

EXAMPLE 17
PREPARATION OF CROSS-LINKED HYALURONIC ACID (HY)
Product Description:
- 10% of carboxy groups used in internal esterification.
- 90% of carboxy groups salified with sodium.

6.21 gr of HY tetrabutylammonium salt with a molecular weight of 170,000 corresponding to 10 mEq of a monomeric unit are solubilized in 248 ml of DMSO at 25° C., 0.118 gr (1 mEq) of pyridine chloride are added and the resulting solution is agitated for 30 minutes.

A solution of 0.16 g (1 mEq) of N-benzyl-N'-ethyl carbodiimmide in 20 ml of DMSO is slowly added drop by drop over a time interval of 1 hour and the mixture is kept at a temperature of 30° C. for 45 hours.

A solution made up of 100 ml of water and 2.5 of sodium chloride is added and the resulting mixture is slowly poured into 750 ml of acetone, maintaining continual agitation. A precipitate is formed which is then filtered 5 and washed three times with 100 ml of acetone/$H_2O$ 5:1 and three times with 100 ml of acetone finally vacuum-dried for 24 hours at a temperature of 30° C.

3.9 grs of the title compound are obtained. Quantitative determination of the total ester groups is carried out according to the saponification method described on pp 169–172 of "Quantitative Organic Analysis Via Functional Groups" 4th Edition John Wiley and Sons Publication.

4. Formulations According to the Invention

EXAMPLE 18
PREPARATION OF AN INJECTABLE SUSPENSION CONTAINING AN ACTIVE PRINCIPLE BASED ON CROSS-LINKED HYALURONIC ACID (ACP)

One 2-ml vial contains:

| | |
|---|---|
| autocross-linked hyaluronic acid (ACP) | 20 mg |
| sodium chloride | 17 mg |
| dihydrate monobasic sodium phosphate | 0.1 mg |
| dodecahydrate bibasic sodium phosphate | 1.2 mg |
| water for injection | 2 ml |

EXAMPLE 19:
PREPARATION OF AN INJECTABLE SUSPENSION CONTAINING AN ACTIVE PRINCIPLE WHICH IS A 75/25 MIXTURE BASED ON AUTOCROSS-LINKED HYALURONIC ACID AND HYALURONIC ACID SODIUM SALT

One 2-ml pre-filled syringe contains:

| | |
|---|---|
| autocross-linked hyaluronic acid (ACP) | 15 mg |
| hyaluronic acid sodium salt (hyalectin) | 5 mg |
| sodium chloride | 17 mg |
| dihydrate monobasic sodium phosphate | 0.1 mg |
| dodecahydrate bibasic sodium phosphate | 1.2 mg |
| water for injection | 2 ml |

EXAMPLE 20
PREPARATION OF AN INJECTABLE SUSPENSION CONTAINING AN ACTIVE PRINCIPLE BASED ON AUTOCROSS-LINKED HYALURONIC ACID VEHICLING AN ANTIINFLAMMATORY AGENT SUCH AS METHYL-PREDNISOLONE 21-SUCCINATE SODIUM SALT

One 2-ml pre-filled syringe contains:

| | |
|---|---|
| autocross-linked hyaluronic acid (ACP) | 20 mg |
| methylpredinsolone 21-succinate sodium salt | 10 mg |
| sodium chloride | 18 mg |
| water for injection | 2 ml |

EXAMPLE 21
PREPARATION OF AN INJECTABLE SUSPENSION CONTAINING AN ACTIVE PRINCIPLE WHICH IS A 75/25 MIXTURE BASED ON AUTOCROSS-LINKED HYALURONIC ACID AND HYALURONIC ACID SODIUM SALT VEHICLING AN ANTIINFLAMMATORY AGENT SUCH AS TRIAMCINOLONE PHOSPHATE SODIUM SALT

One 2-ml vial contains:

| | |
|---|---|
| autocross-linked hyaluronic acid (ACP) | 15 mg |
| hyaluronic acid sodium salt (Hyalectin) | 5 mg |
| triamcinolone phosphate sodium salt | 20 mg |
| sodium chloride/ 18 | mg |
| water for injection | 2 ml |

5. Teats on Formulations According to the Invention

EXAMPLE 22
PREPARATION OF AN ACP/HA FORMULATION IN WHICH THE ACP COMPONENT IS AUTOCROSS-LINKED TO A NOMINAL DEGREE OF 5%

HA with a molecular weight range of 500–730 KDa was cross-linked to a nominal level of 5%.

ACP/HA formulations were prepared at a final concentration of 1% w/w in phosphate buffer (NaCl 0.15M, phosphate salts 0.002M) at pH=6.5, by mixing various proportions of ACP/HA, ranging from 0/100 to 100/0 %. The suspensions were allowed to swell for 24 hours.

The rheological properties of the ACP/HA mixtures were measured on a Rheometrics Fluid Spectrometer (RFS-8500) fitted with several geometries (50 mm diameter parallel plates: 1 mm or 2 mm gap and Couette: cup diameter 34 mm, bob diameter and length 32 respectively) at the fixed temperature of 25° C. From the oscillatory shear measurements (typically at 10% strain value), the viscoelastic parameters G' (storage modulus), G" (loss modulus) and $\eta^*$ (complex viscosity) were obtained over the frequency range of 0.01–100 rad/sec.

Figure 2A:
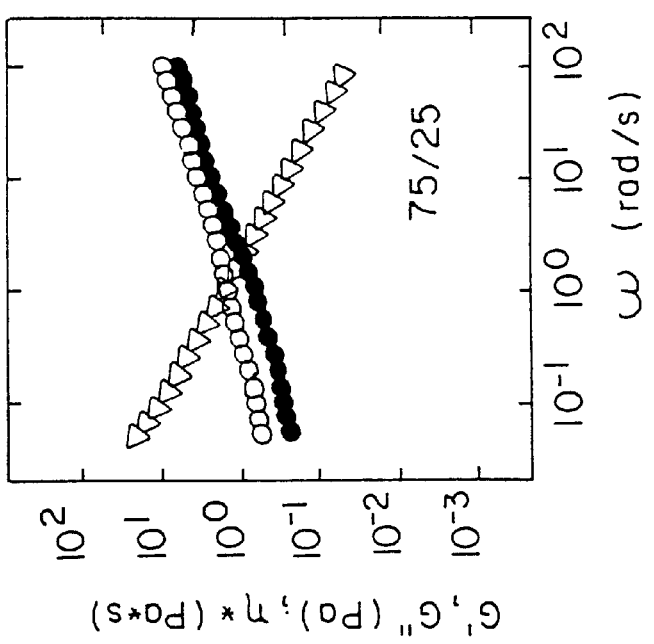
FIGS. 2A–2D show viscoelastic spectra for different relative proportions of ACP/HA-mixtures in phosphate buffer, Cp=1% w/w, T=25° C. (G'(°) ;G",(.); η*, (∇)

The measurements indicated that ACP's, dispersed at sufficiently high polymer concentration and swollen in aqueous media, produce viscoelastic and transparent solid-like systems. The viscoelastic spectrum reported in FIG. 2A (ACP/HA 100/0) clearly shows a gel-like behaviour. In particular, $G'(\omega) > G''(\omega)$ in the whole range of frequencies investigated and both G' and G" are slightly frequency-dependent. The ratio G'/G" (tan) reaches a constant value (0.3) for frequencies lower than 2 rad/sec and it increases slightly (up to 0.4) with increasing frequency. The complex viscosity, $\eta^*$, is strongly frequency-dependent following a power law in the whole range of frequencies investigated. The apparent power law exponent is $\approx -0.82$.

By using the same applied strain (0.1 strain units), the measured absolute values of both moduli and complex viscosity, but not the viscoelastic behaviour, are appreciably affected by the geometry used. This finding reflects the non-homogeneous character of the system. The gel-like response of ACP (100/0) is very different from the entangled network behaviour typical of the HA starting material (Kobayashi Y. et al. Biorheology, 1994, 31, 235–244).

Figure 2B:
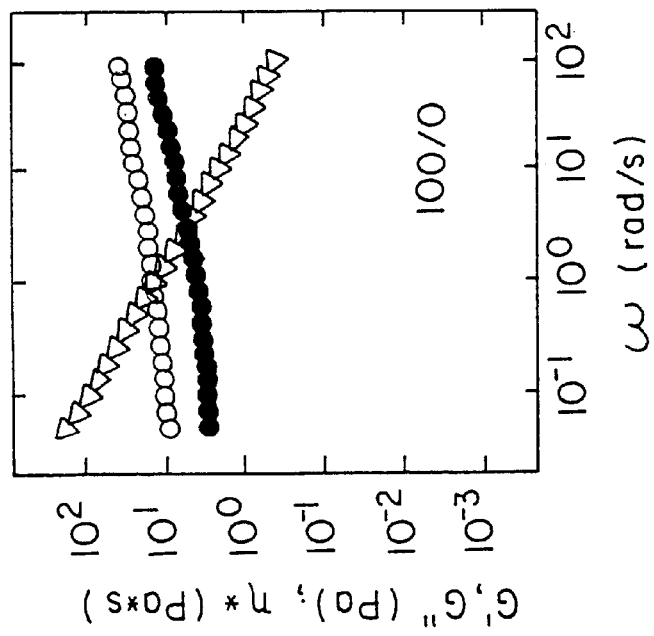
Figure 2C:
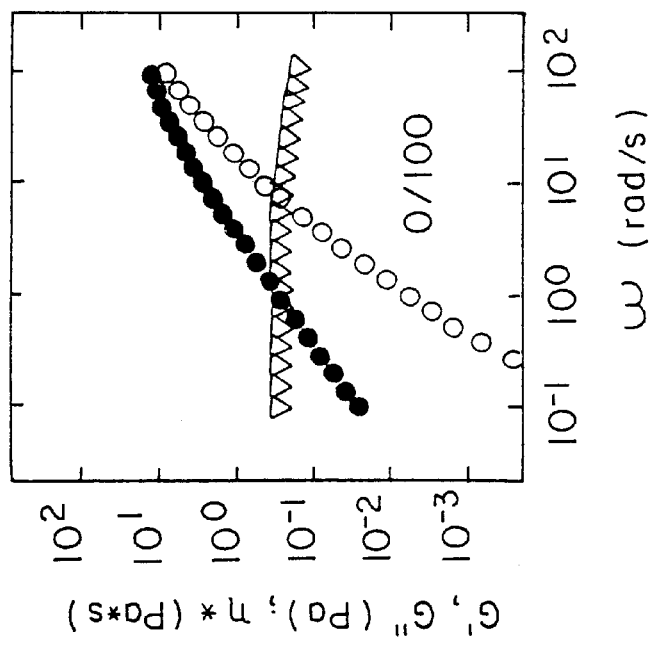
Figure 2D:
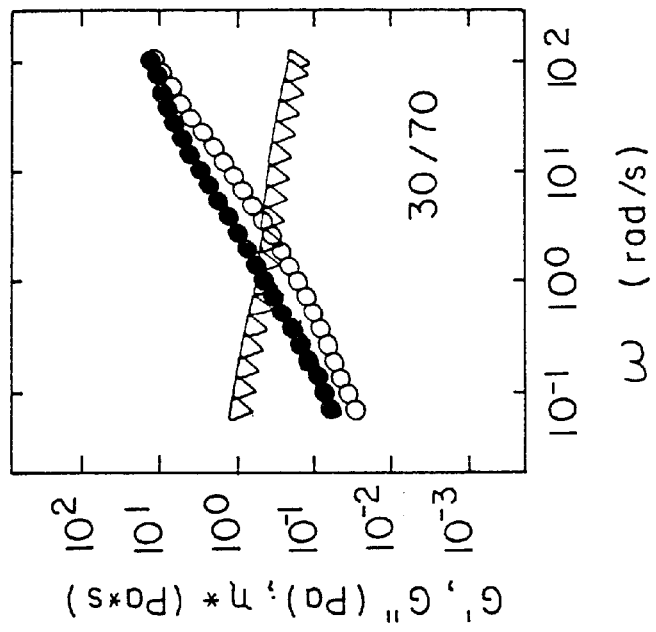

As shown in FIG. 2D (ACP/HA 0/100), the mechanical spectrum shows $G''(\omega) > G'(\omega)$ and in the terminal region $G' \alpha \omega 2$ and $G'' \alpha \omega$. Moreover, $\eta^*(\omega)$ is essentially independent from the frequency. By blending the two polymers in different ratios, while maintaining constant the total polymer concentration (1% w/w), it is possible to obtain a wide range of 2-component systems. In particular, a HA-rich mixture (ACP/HA 30/70) may be regarded as a suspension in which the disperse component is constituted by discrete particles of swollen ACP and the continuous component is the HA aqueous solution. Conversely, the ACP-rich mixture (ACP/HA 75/25) may be considered as a "composite" in which the continuous component is much more rigid than the disperse component constituted by the HA aqueous solution.

The mechanical response of such systems is expected to be dominated by the viscoelastic properties of the continuous component. In fact, the viscoelastic spectrum of the HA-rich mixture (FIG. 2C, 30/70) shows a liquid-like behaviour in the whole range of frequency investigated. However, in comparison with HA alone (FIG. 2D), G' and G" are enhanced (remarkable increase in the case of G') especially in the terminal region where the frequencies corresponding to joint movements at ordinary walking speed are included. On the other hand, the viscoelastic spectrum of the ACP-rich mixture (FIG. 2B, 75/25) shows a gel-like behaviour similar to that of ACP alone but with a decrease of both moduli especially at low frequency. In this case, G' and G" show a higher frequency-dependence. The changes at low frequency observed for both mixtures reflect the enormous differences between the moduli of the two components in the medium.

Figure 3:
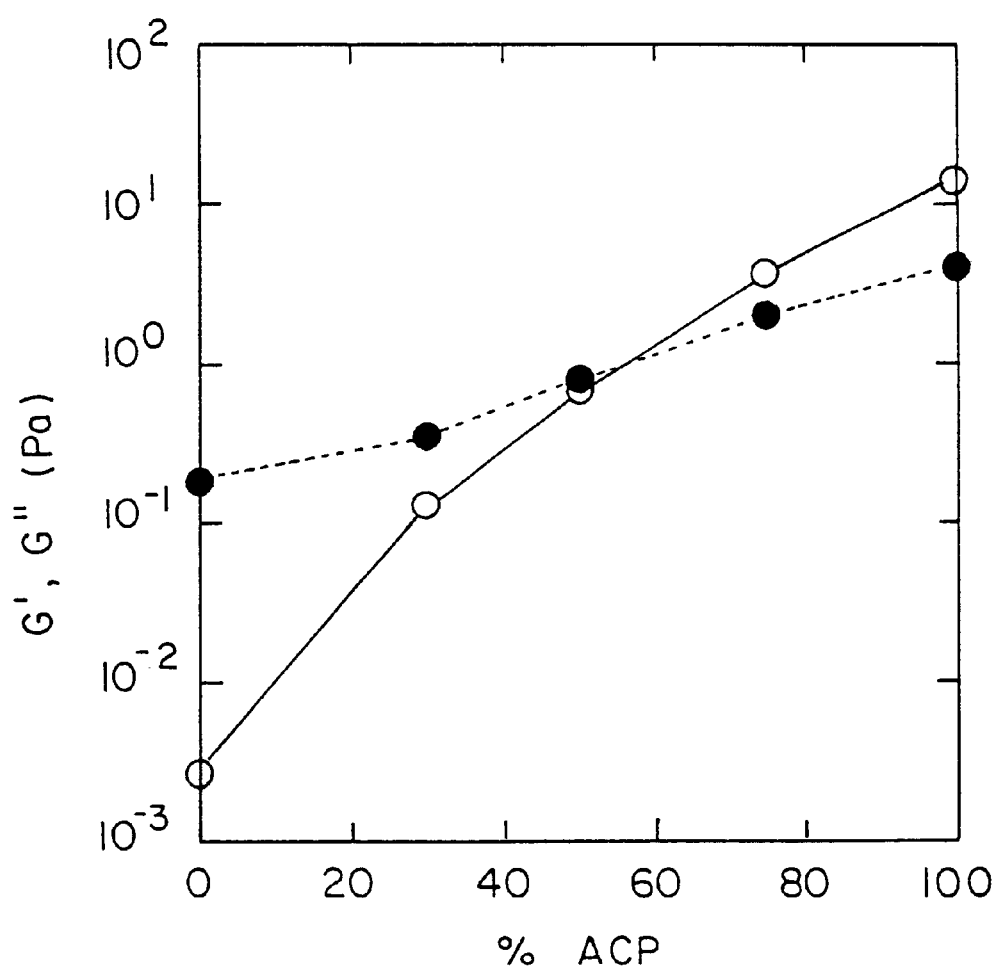
FIG. 3 shows storage modulus (G') (°) and loss modulus (G") (.) as a function of ACP content (%). Frequency =0.72 rad/s (corresponding to the movement of the joint at normal walking pace), T=25° C.

As clearly shown in FIG. 3, at the frequency corresponding approximately to the movement of the joint in walking (0.72 rad/sec) (Kobayashi et al, Biorheology, 1994, supra), and at T=25° C., G' and G" cross each other as function of the ACP content in the mixtures. In particular, a "transition" from liquid-like to solid-like behaviour occurring approximately in correspondence to 50% w/w of ACP content in the mixture is evident.

Figure 4:
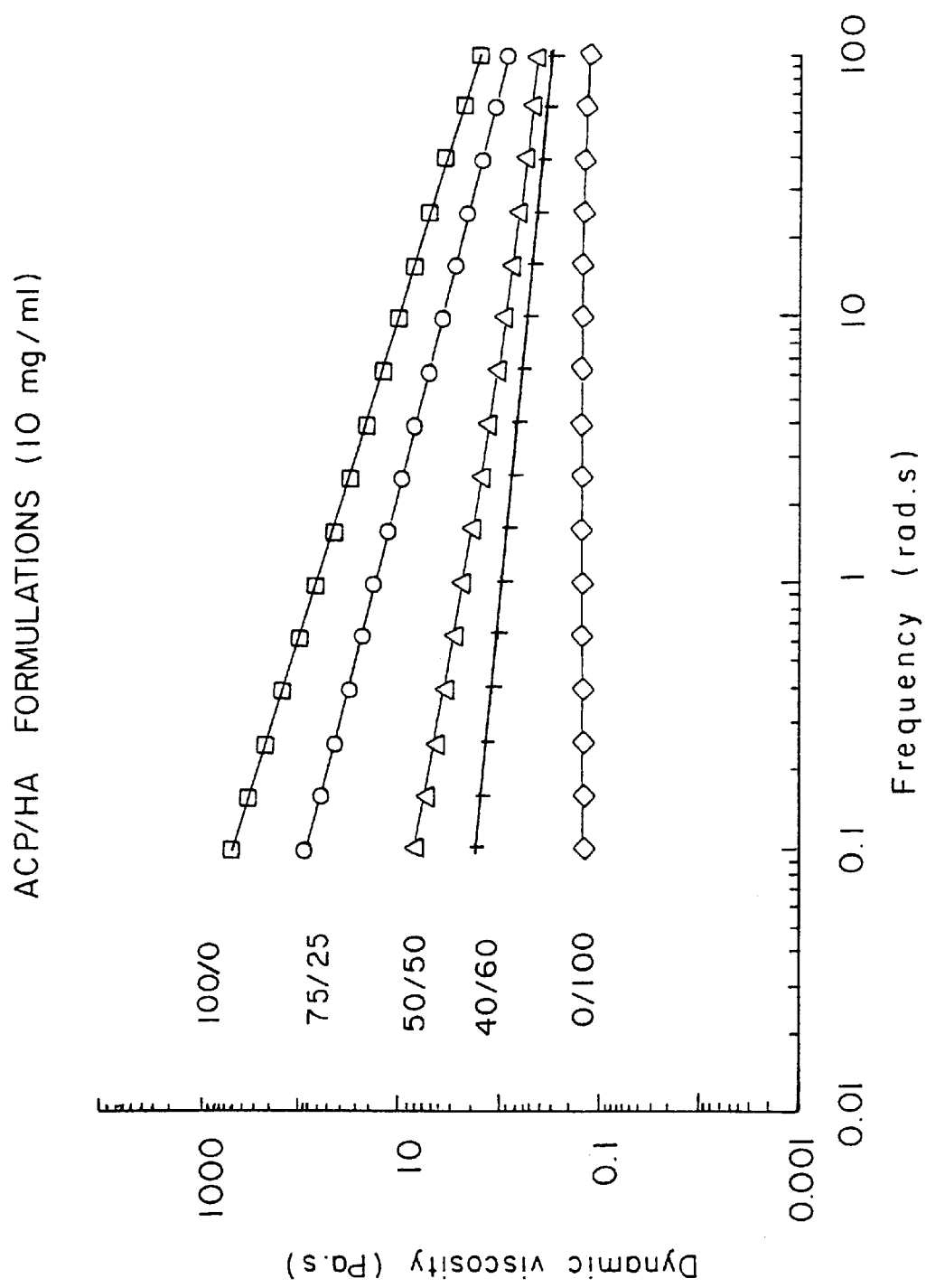
FIG. 4 shows a comparison of the dynamic viscosities of formulations of ACP/HA at various ratios.

FIG. 4 shows a comparison of the dynamic viscosity of ACP/HA formulations with ACP/HA ratios ranging from 100/0 to 0/100. The improvement in the viscoelastic properties of the compositions with increasing content of ACP is clearly apparent.

EXAMPLE 23
PREPARATION AND TESTING OF ACP/HA FORMULATIONS IN WHICH THE ACP COMPONENT IS AUTOCROSS-LINKED TO VARYING DEGREES.

Autocross-linked carboxyl polysaccharides (ACP) synthesized from hyaluronic acid (HA) (640,000 Da) and used to prepare mixtures of ACP/HA included the following:

| | |
|---|---|
| ACP 20% | 0.5% $H_2O$ |
| ACP 10% | 0.5% $H_2O$ |
| ACP 5% | 0.5% $H_2O$ |

The values 20, 10 and 5% refer to the nominal percentage of esterification, while 0.5% indicates the quantity of water added during synthesis.

The formulations were prepared by mixing different quantities of ACP and HA (640,000 Da) in phosphate buffer (NaCl 0.15M and phosphate salts 0.002M) at pH=6.5. The mixtures all had final concentrations of 10 mg/ml and were prepared in a range of ACP/HA ratios of 100/0–0/100%. The suspensions were left to swell for 24 hours and then filtered on glass filters with a pore size of 100–40 $\mu$m.

Rheological measurements were made with a "Fluid Spectrometer RFS 8500" rheometer (Rheometrics). Geometries were selected according to the viscosity of the solution: parallel plates (2 mm gap) for fairly viscous solutions and Couette (1 mm gap) for only slightly viscous-solutions.

The studies were performed in dynamic frequency sweep (range=100–0.05 rad/sec. strain=10%, T=25° C.).

Figure 5:
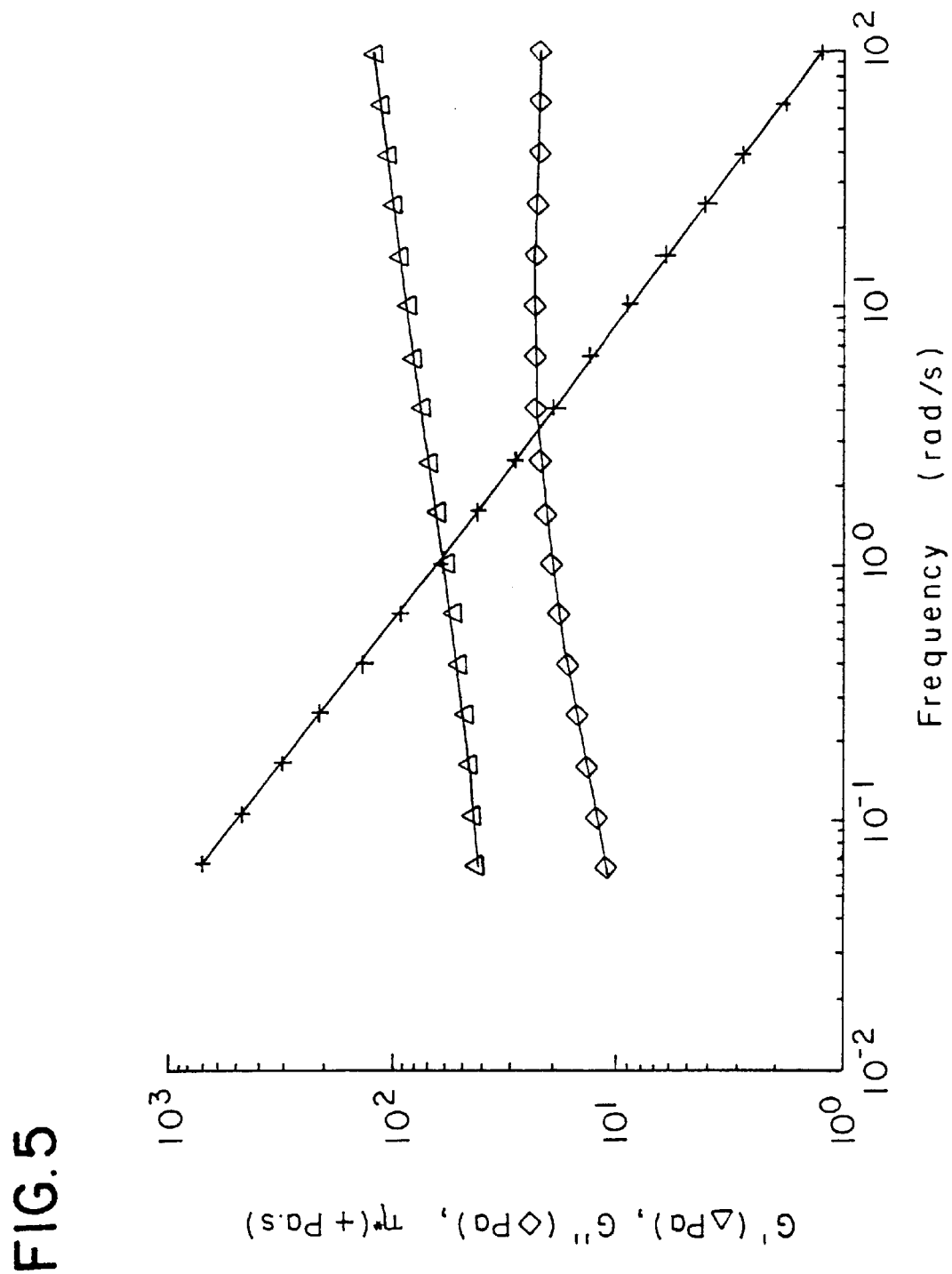
FIG. 5 shows viscoelastic spectrum of a formulation of ACP/HA, 100/0; ACP 20%, 0.5% $H_2O$.
Figure 6:
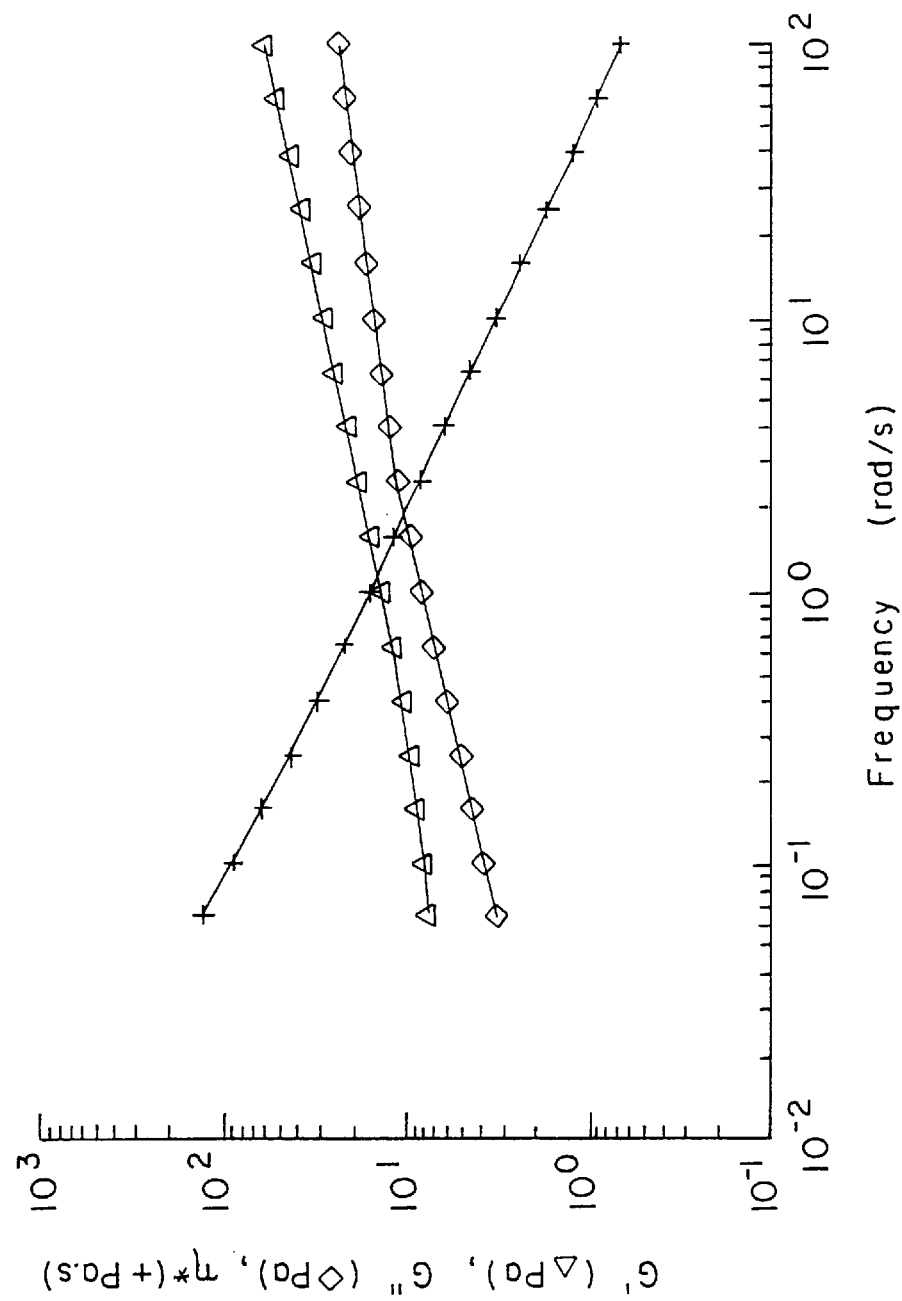
FIG. 6 shows viscoelastic spectrum of a formulation of ACP/HA, 75/25; ACP 20%, 0.5% $H_2O$.

Formulations constituted by ACP/HA at 100/0 are generally characterized by G' being higher than G" for the whole range of frequencies considered (FIG. 5). While maintaining the degree of cross-linking constant, the addition of greater amounts of HA in the mixture results in lower viscosity values, while G' and G" tend to get closer together (FIG. 6).

Figure 7:
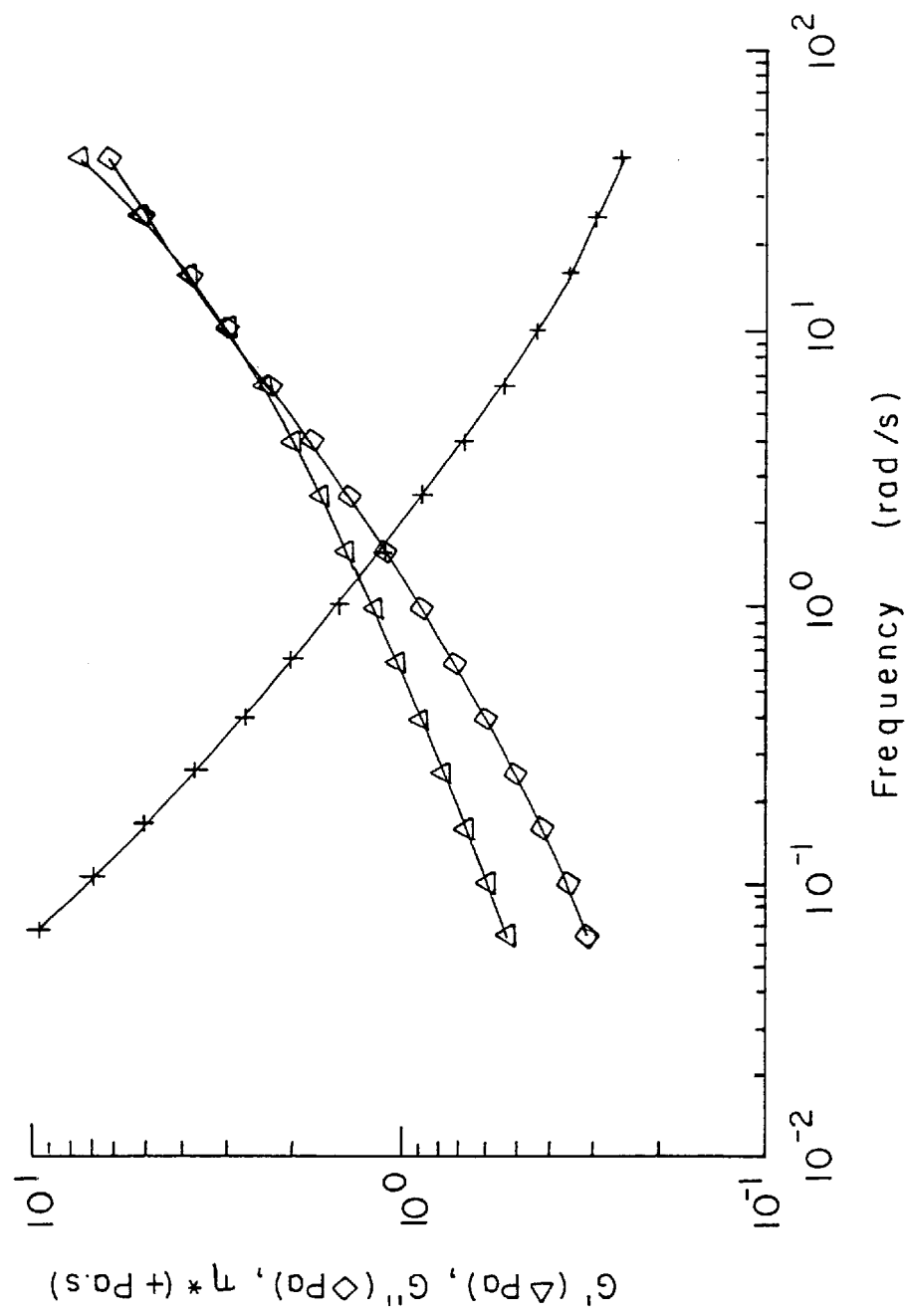
FIG. 7 shows viscoelastic spectrum of a formulation of ACP/HA, 50/50; ACP 5%, 0.5% $H_2O$.
Figure 8:
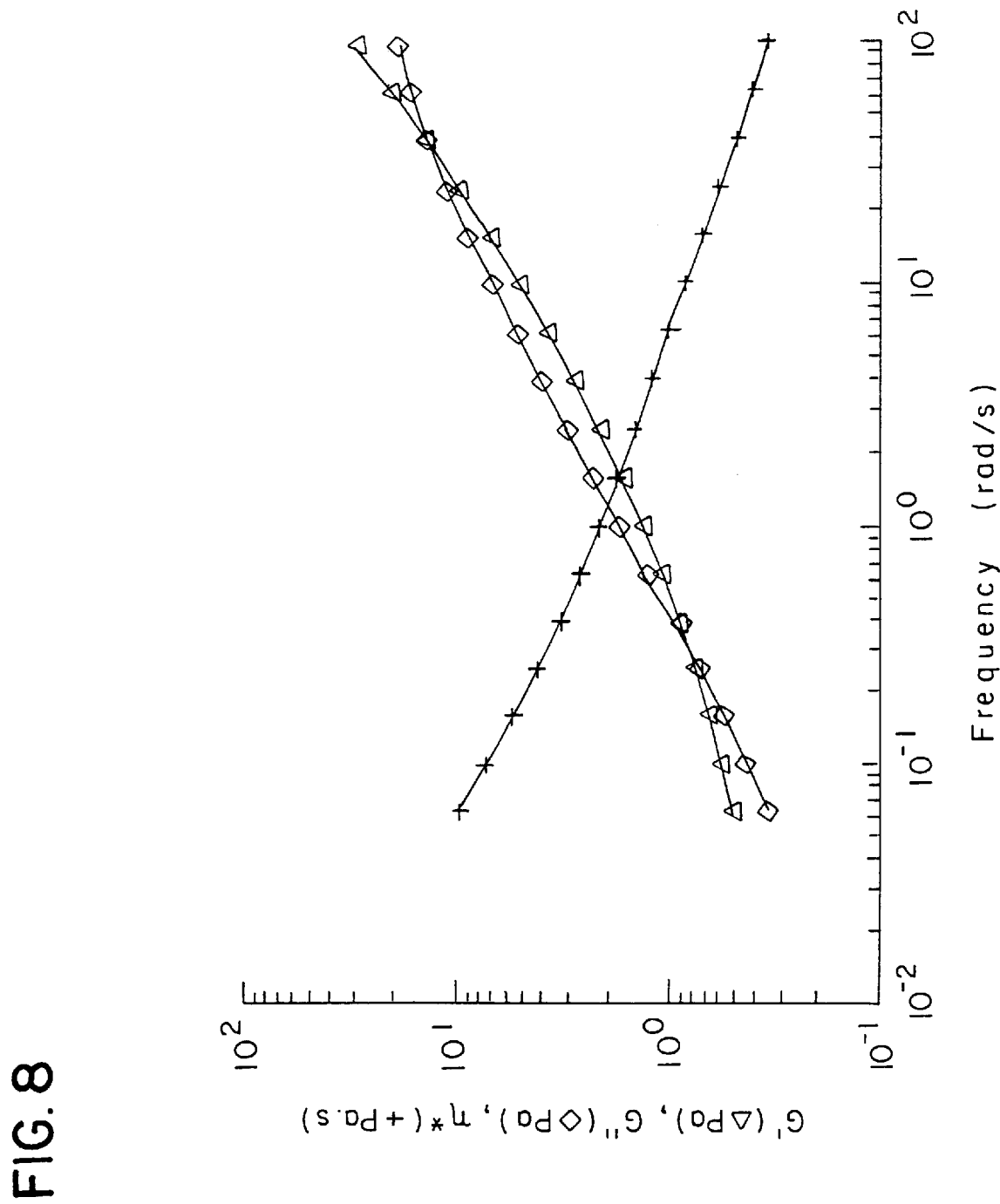
FIG. 8 shows viscoelastic spectrum of a formulation of ACP/HA, 50/50; ACP 20%, 0.5% $H_2O$.

Particularly in the case of formulations of an ACP content of 50%, G' and G" may, according to the type of ACP being studied, overlap or cross over in correspondence to one or two different frequencies (FIGS. 7, 8).

Figure 9:
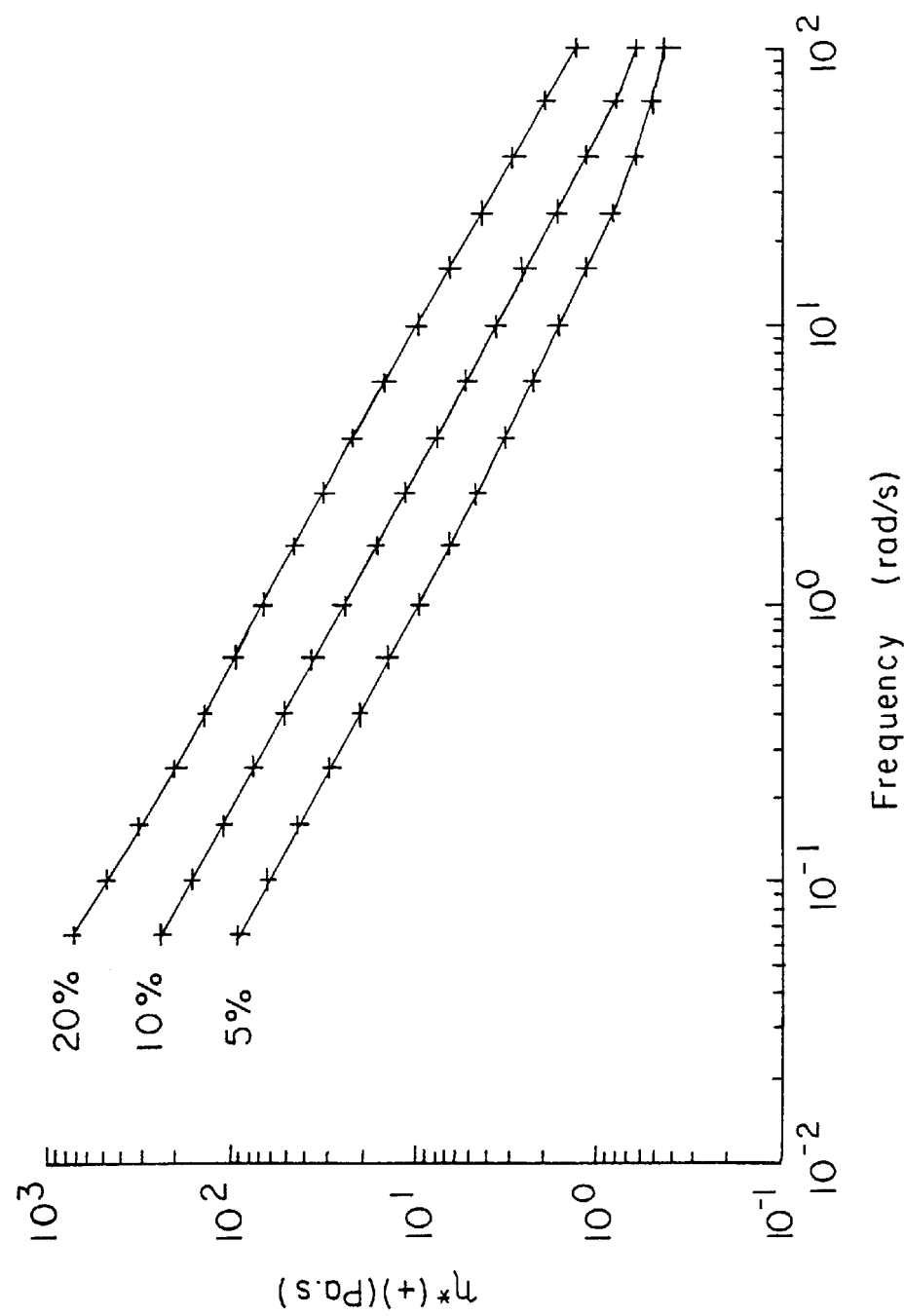
FIG. 9 shows a comparison of the dynamic viscosities of formulations of ACP/HA, 100/0; ACP 20%, 10%, and 5%, 0.5% $H_2O$.
Figure 10:
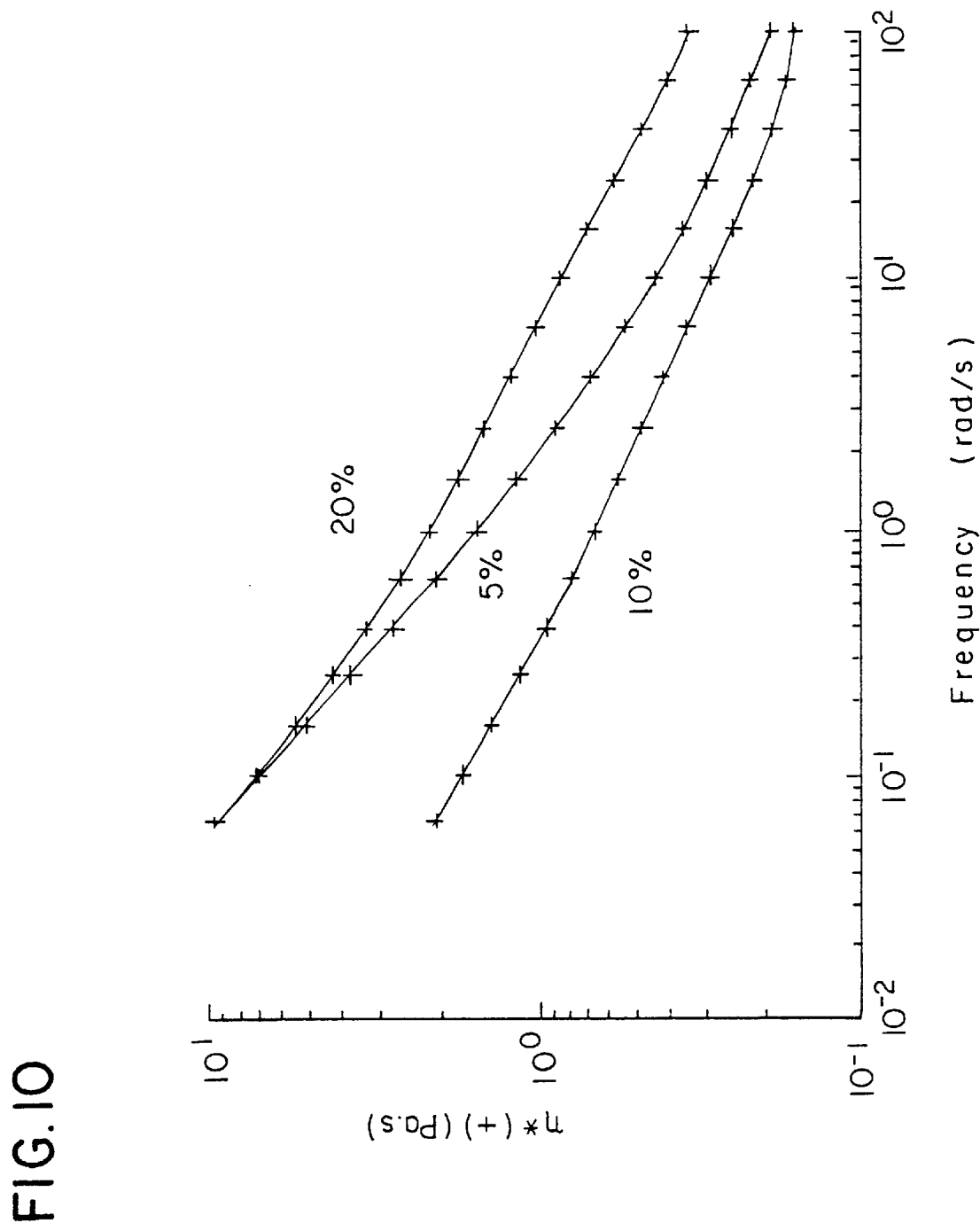
FIG. 10 shows a comparison of the dynamic viscosities of formulations of ACP/HA, 50/50; ACP 20%, 10%, and 5%, 0.5% $H_2O$.
Figure 11:
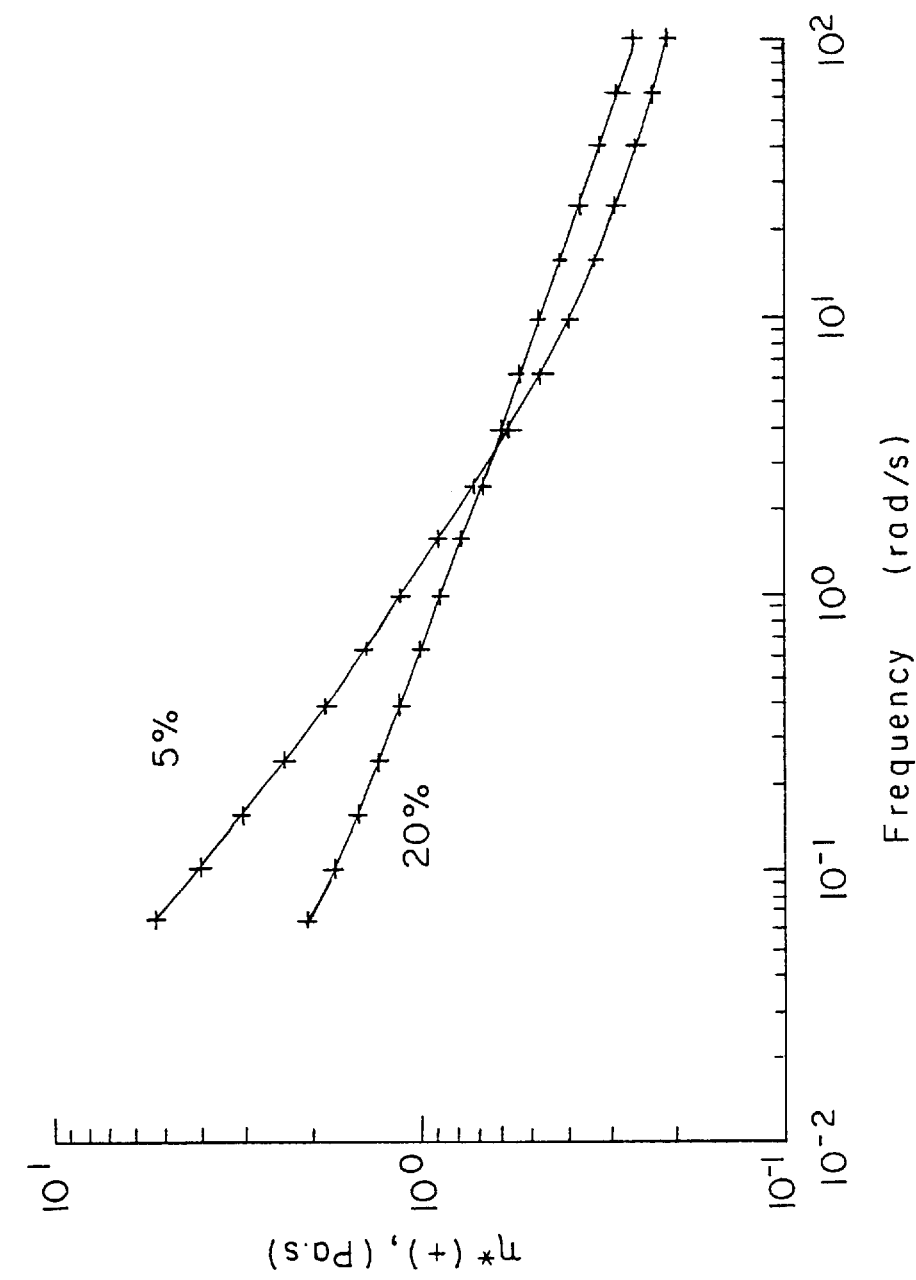
FIG. 11 shows a comparison of the dynamic viscosities of formulations of ACP/HA, 40/60; ACP 20% and 5%, 0.5% $H_2O$.

FIGS. 9, 10, and 11 show the effect of the percentage of esterification on the viscosity of ACP/HA formulations with different ACP/HA ratios.

It is possible to conclude, from the viscoelastic spectra, that for ACP/HA formulations with a high ACP content (eg 100/0), the viscosity pattern is of the 20%>10%>5% type (FIG. 9), while for 50/50 mixtures, the result is 20%>5%>10% (FIG. 10). Lastly, mixtures of ACP/HA 40/60, starting from ACP 20% and ACP 5%, present only slight differences in viscosity (FIG. 11).

If the objective is to reach high viscoelasticity values, ACP with a high degree of cross-linking (ACP 20%) alone (100/0) or mixed with small quantities of hyaluronic acid (e.g. 75/25) should be used. If, on the other hand, the desired viscoelasticity values are not high, (ACP/HA 40/60, 30/70), then the percentage of cross-linking is a less decisive factor.

The results described above indicate that the cross-linking of HA to form ACP yields a HA derivative with viscoelastic properties which are superior to those of unmodified HA. In addition, the Theological properties of ACP can be modulated by preparing compositions consisting of ACP/HA mixtures at varying weight/weight ratios.

Even though ACP formulated in pharmaceutical excipients presents gel-like rheological profiles, interesting results have been obtained by mixing different quantities of ACP 10% 100/0 with synovial fluid from non-osteoarthritic horses.

Figure 12:
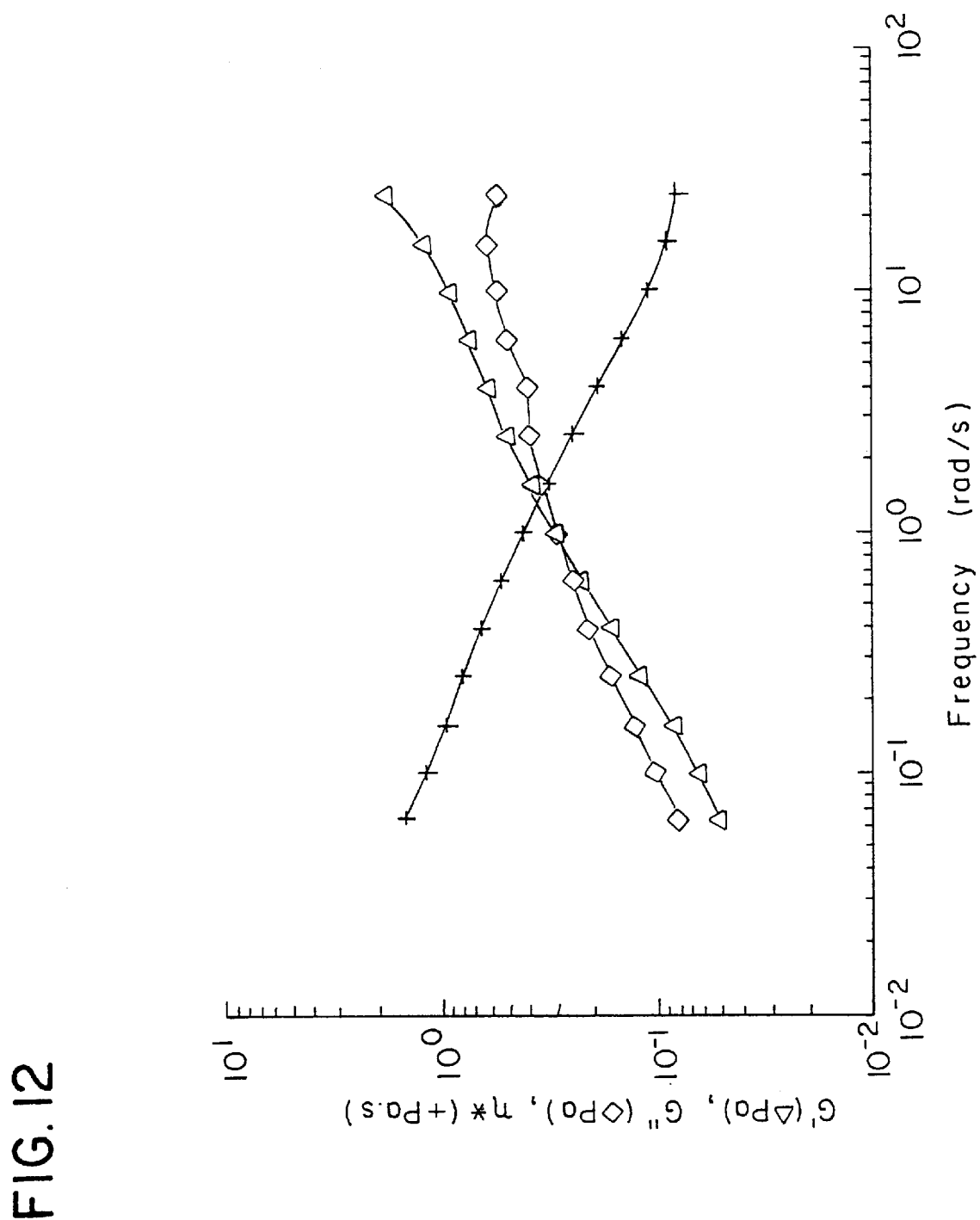
FIG. 12 shows viscoelastic spectrum of synovial fluid from a non-osteoarthritic horse.
Figure 13:
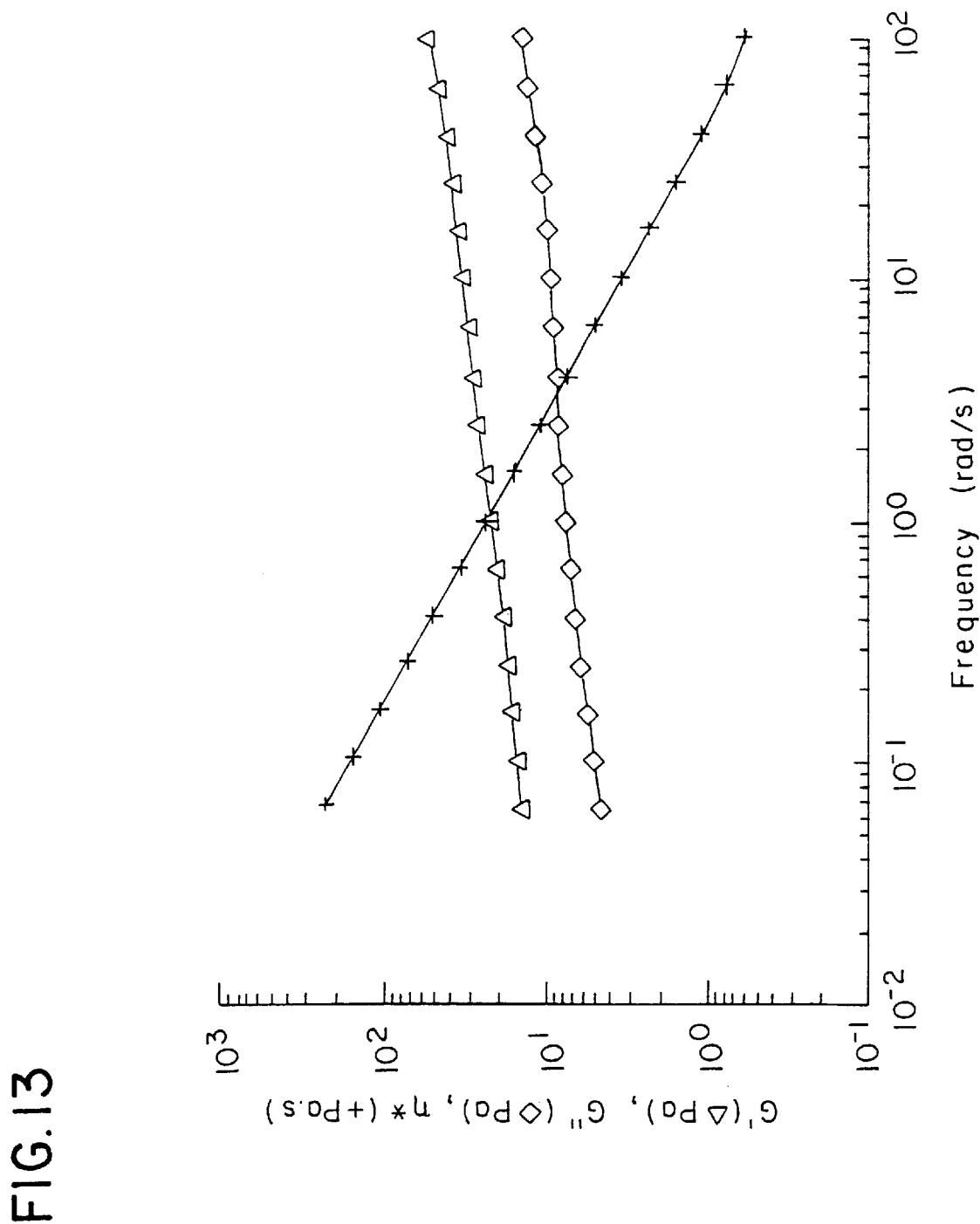
FIG. 13 shows viscoelastic spectrum of ACP/HA, 100/0; ACP 10%, 0.5% $H_2O$.

FIGS. 12 and 13 show respectively the Theological profiles of equine synovial fluid and ACP 10% 100/0 formulated in pharmaceutical excipients at a concentration of 10 mg/ml.

Figure 14:
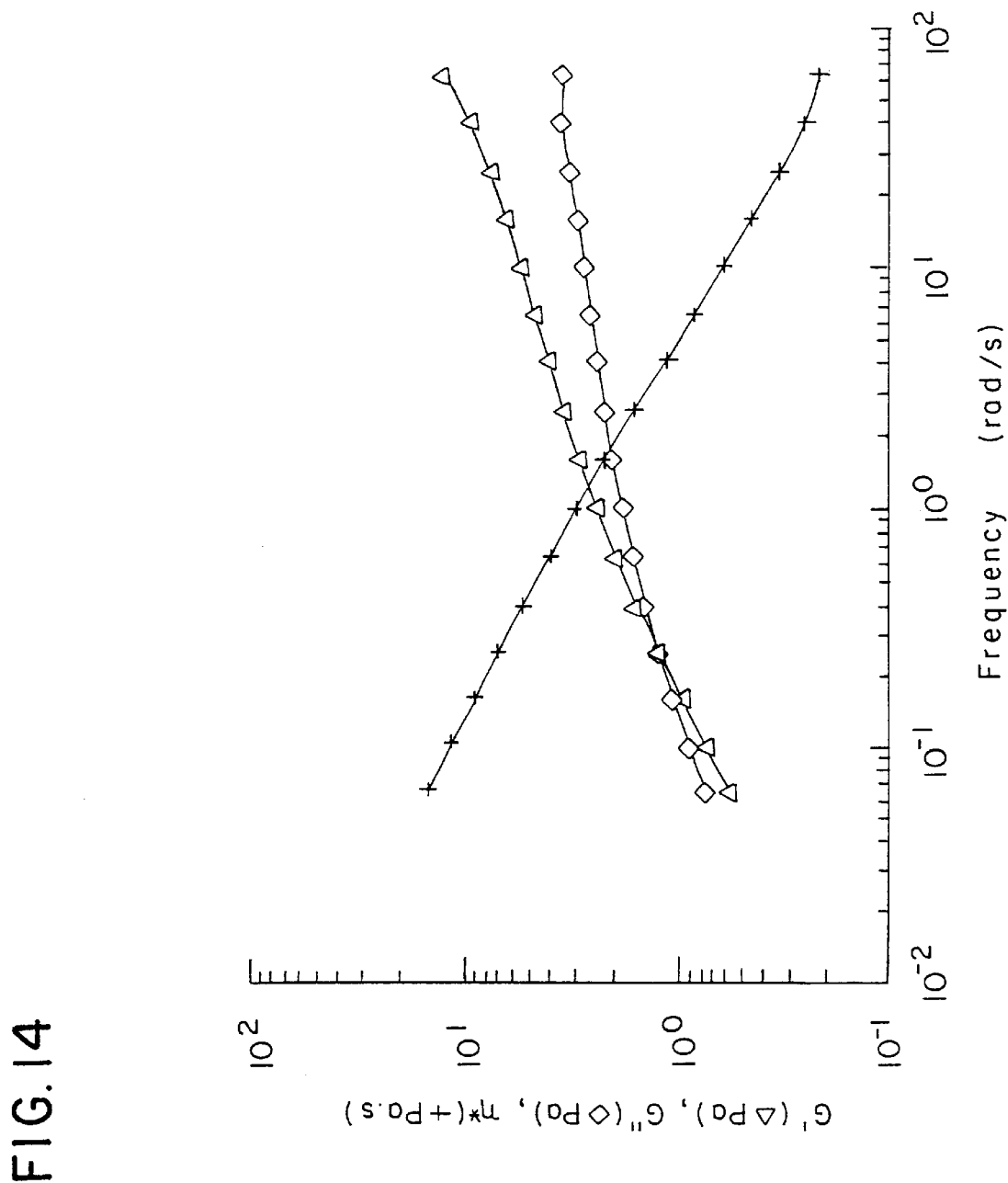
FIG. 14 shows viscoelastic spectrum of synovial fluid from a non-osteoarthritic horse with the addition of ACP 100/0, 10% 0.5% $H_2O$, 3.3 mg/ml.
Figure 15:
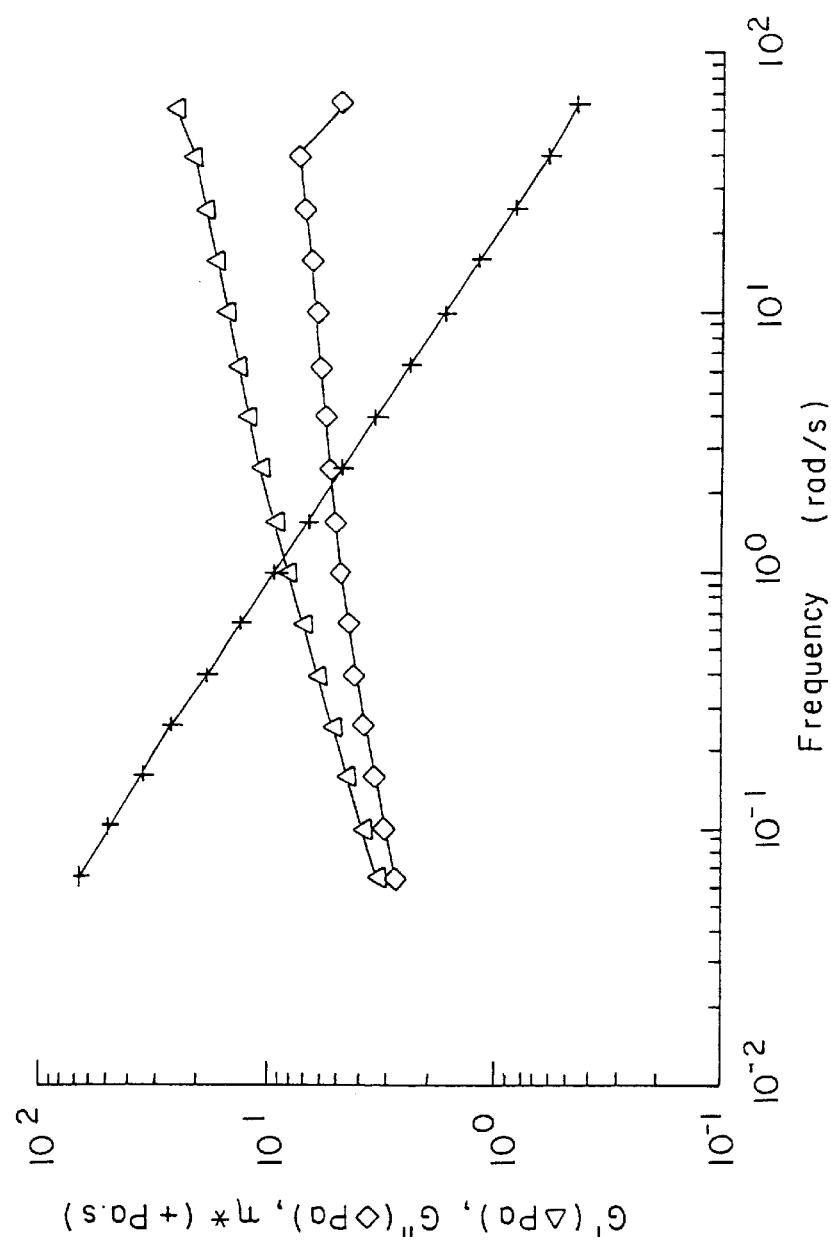
FIG. 15 shows viscoelastic spectrum of synovial fluid from a non-osteoarthritic horse with the addition of ACP 100/0, 10% 0.5% $H_2O$, 5.5 mg/ml.

Mixtures of ACP 10% with synovial fluid at final concentrations of 3.3 and 5 mg/ml of ACP gel (FIGS. 14 and 15) show not only a decisive increase in all viscoelastic parameters when compared to synovial fluid alone, but also a theoretically ideal Theological profile when compared to that of ACP alone. Indeed, G' and G" which run parallel in ACP-based formulations, cross over or tend to cross over in the presence of synovial fluid, according to the quantity of ACP added.

These results indicate that, surprisingly, the addition of ACP to synovial fluid at a concentration which would be expected to exist following injection of ACP pharmaceutical compositions into articular joints, could modify the typical Theological profile of ACP's.

EXAMPLE 24
COMPARISON OF THE VISCOELASTIC PROPERTIES OF ACP AND EXISTING COMMERCIAL HA-BASED PRODUCTS FOR THE TREATMENT OF OSTEOARTHRITIS BY INTRA-ARTICULAR INJECTION

The HA-based products currently on the market and used to treat arthropathies by intraarticular injection include:

ARTZ (Seikagaku, Japan), an HA-based formulation with a molecular weight of between 600,000 and 1,200,000 Da;

SYNVISC (Biomatrix, U.S.A.), a two-component system composed of a mixture of two cross-linked HA derivatives, hylan fluid and hylan gel (US 4,713,448).

HYALGAN (Fidia), an HA-based formulation with a molecular weight of between 500,000 and 730,000 (EP 0138572 B1).

Figure 16:
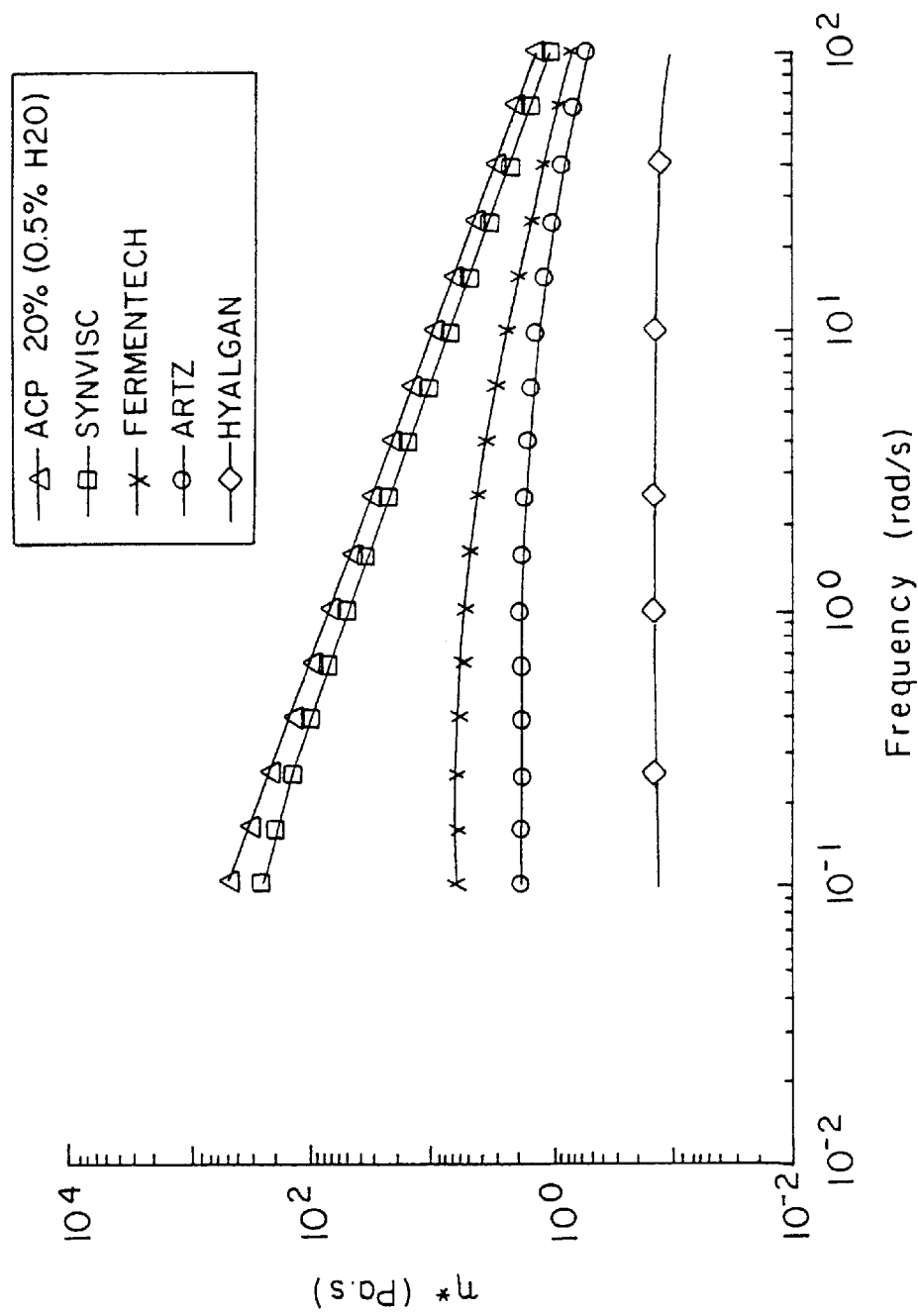
FIG. 16 shows a comparison of the dynamic viscosities of ACP, Synvisc, Fermentech, Artz and Hyalgan.

The dynamic viscosity of ACP 20%, 0.5% water was compared to that of the above pharmaceutical products. The four formulations all had similar characteristics with respect to the final HA concentration and the pharmaceutical excipients present. The results of this comparison are shown in FIG. 16 and indicate that the ACP formulation has superior dynamic viscosity when compared to the three commercially available products.

The development of ACP/HA pharmaceutical compositions was designed to provide compositions with improved viscoelastic properties, and consequently increased joint residence times, with respect to the presently available commercial HA-based products for the treatment of arthropathies. The variation of the ratio of ACP and HA contained in these compositions also permits the preparation of pharmaceutical compositions which have the optimal Theological properties for the treatment of arthropathies of various origins.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition for the treatment of arthropathies comprising:
   a) an autocross-linked hyaluronic acid,
   b) a noncross-linked hyaluronic acid, wherein the ratio of component (a) to component (b) is 5:95, and
   c) a pharmaceutically acceptable excipient, diluent or carrier.

2. The pharmaceutical composition of claim 1, further comprising a pharmacologically active substance.

3. The pharmaceutical composition of claim 1 or, 2, wherein the autocross-linked hyaluronic acid is synthesized form hyaluronic acid having a molecular weight range from 50 to 5,000 kDa and has a level of cross-linking between 1% to 30% with respect to (he carboxyl groups.

4. The pharmaceutical composition of claim 2, wherein the pharmacologically active substance is an antibiotic.

5. The pharmaceutical composition of claim 2, wherein the pharmacologically active substance is a steroidal anti-inflammatory agent.

6. The pharmaceutical composition of claim 2, wherein the pharmacologically active substance is a non-steroidal anti-inflammatory agent.

7. The pharmaceutical composition of claim 2, wherein the pharmacologically active substance is an anaesthetic, an epitheliotrophic vitamin, a hormonal-type anti-inflammatory or analgesic agent, a cytokine, a cytokine receptor, or a growth factor.

8. A method of treatment which comprises administering intra-articularly to a patient affected by arthropathy an effective amount of the pharmaceutical composition of claim 1 or 2.

* * * * *